| United States Patent [19]
Tam et al.

[11] Patent Number: 4,507,230
[45] Date of Patent: Mar. 26, 1985

[54] PEPTIDE SYNTHESIS REAGENTS AND METHOD OF USE

[75] Inventors: James P. Tam; William F. Heath, Jr., both of New York, N.Y.; Robert B. Merrifield, Cresskill, N.J.

[73] Assignee: Research Corporation, New York, N.Y.

[21] Appl. No.: 377,443

[22] Filed: May 12, 1982

[51] Int. Cl.$^3$ .................... C07C 103/52; C08L 89/00
[52] U.S. Cl. ............................ 260/112.5 R; 525/54.11
[58] Field of Search ................ 424/177; 260/112.5 R; 525/54.11

[56] References Cited

U.S. PATENT DOCUMENTS 4,062,815  12/1977  Hughes et al. ..................... 424/177

OTHER PUBLICATIONS

Tam et al., *J. Am. Chem. Soc.*, 105(21), 6442–6455, (1983).
Lenard et al., *J. Am. Chem. Soc.*, 89:1, pp. 181–182, (1967).
*Chemical Abstracts*, 73, 383 (1970), Abstract No. 88152s.
*The Merck Index*, 9th ed., Merck and Co. Inc., Rahway, N.J. 1976.
Solomons, *Organic Chemistry*, John Wiley and Sons, N.Y. p. 650, (1978).
Yoshihiro et al., *Bull. Chem. Soc. Jpn.*, 53, 464–468, (1980).

*Primary Examiner*—Delbert R. Phillips
*Assistant Examiner*—F. Moezie
*Attorney, Agent, or Firm*—Scully, Scott, Murphy & Presser

[57] ABSTRACT

A method of releasing a functional group present in an amino acid or amino acyl residue from a resin or protecting residue which is bonded to the functional group by a linkage having proton affinity, which comprises: reacting the functional group bonded to the organic residue, with a mixture of HF and a base for a time and under conditions effective to produce the release; wherein the amounts of HF and base in the mixture are adjusted so that said release occurs substantially by an $S_N2$ mechanism.

19 Claims, 14 Drawing Figures

COMPOSITION OF GENERALIZED TERNARY SYSTEM (HF-SOLVENT-BASE) IN $S_N1$ AND $S_N2$ CLEAVAGES OF Tyr (Bzl)

VARYING BEHAVIOR OF WEAK BASES IN TERNARY SYSTEM (HF-TRIFLUOROACETIC ACID-SULFIDE)

EFFECT OF POTENTIATING AND DEACTIVATING SOLVENTS
IN A TERNARY SYSTEM (HF-SOLVENT-DIMETHYLSULFIDE)

DEPENDENCE OF THE RATE OF DEPROTECTION OF
Ser(Bzl) ON THE CONCENTRATION OF HF IN DMS

DEPENDENCE OF DEPROTECTION OF D-BENZYLTYROSINE ON THE CONCENTRATION OF HF IN DMS

DEPENDENCE OF DEPROTECTION OF $N^i$-FORMYL TRYPTOPHAN ON CONCENTRATION OF HF IN DMS

DEPENDENCE OF METHIONINE SULFOXIDE REDUCTION ON % VOLUME OF HF IN DMS

HPLC ANALYSIS OF CRUDE C-TERMINAL PENTAGASTRIN AMIDE

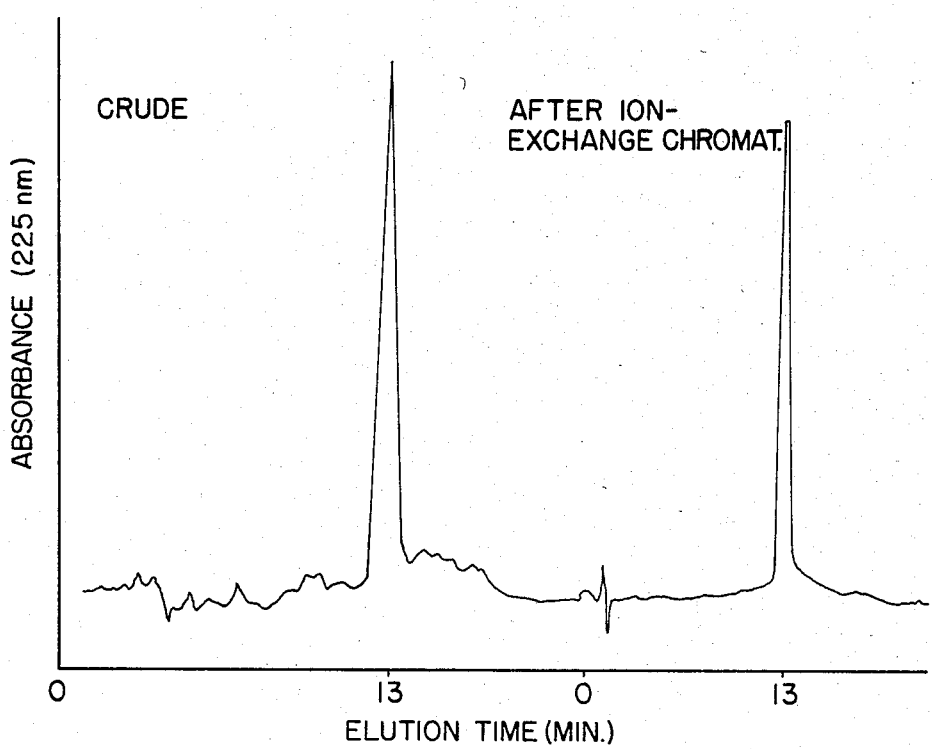
FIG.9A HPLC ANALYSIS OF CRUDE CECROPIN A(1-33)
FIG.9B HPLC ANALYSIS OF PURIFIED CECROPIN A(1-33)
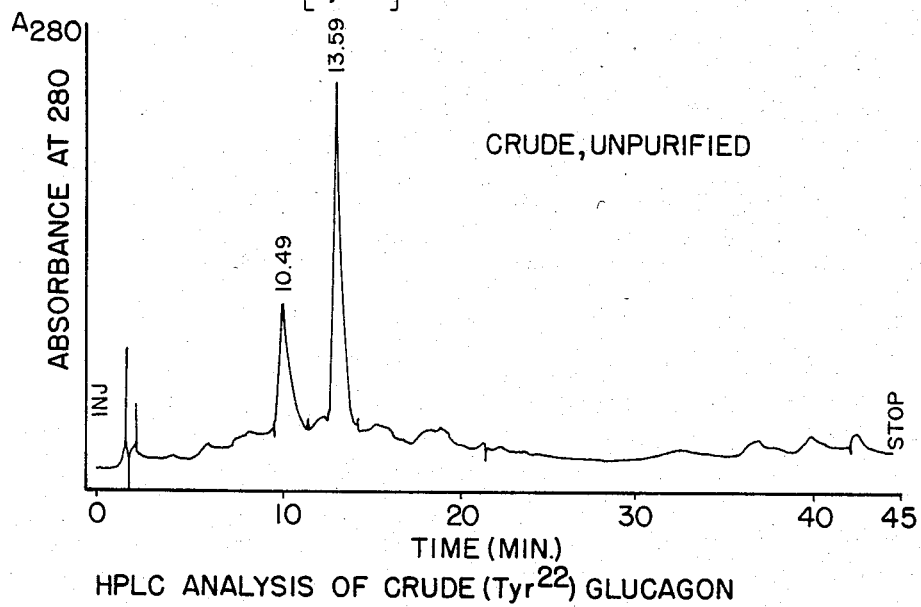
FIG.10 HPLC ANALYSIS OF CRUDE (Tyr$^{22}$) GLUCAGON CM-52 CHROMATOGRAPHIC ANALYSIS OF CRUDE (Tyr$^{22}$) GLUCAGON AFTER HF CLEAVAGE BY CONVENTIONAL METHOD

PEPTIDE SYNTHESIS REAGENTS AND METHOD OF USE

BACKGROUND OF THE INVENTION

Work leading to this invention was sponsored by the National Institutes of Health, of the U.S. Government Department of Health and Human Services.

1. Field of the Invention

The present invention relates to improved deprotection reagents used in peptide synthesis, especially in automated solid-phase peptide synthesis.

2. Brief Description of the Prior Art

The synthesis of peptides is generally carried out through the condensation of the carboxyl group of an amino acid, and the amino group of another amino acid, to form a peptide bond. A sequence can be constructed by repeating the condensation of individual amino acid residues in stepwise elongation, or, in some cases, by condensation between two preformed peptide fragments (fragment condensation). In such condensations, the amino and carboxy groups that are not to participate in the reaction must be blocked with protecting groups which should be readily introduced, be stable to the condensation reactions and be removed selectively from the completed peptide. If a peptide involves amino acids with side chains that may react during condensation, the problem of protection becomes increasingly difficult. A great range of reactive groups and side chains—amino, carboxy, thiol, hydroxy, and so on—must be adequately blocked. Their blocking must be stable to unmasking of the $\alpha$-amino or $\alpha$-carboxy block for stepwise condensation, and must be readily removed at the final stage, leaving the completed peptide moiety intact.

A successful synthesis for a large peptide by a linear strategy must achieve nearly quantitative recoveries for each chemical step. This demanding requirement has been met by solid-phase peptide synthesis, pioneered by R. B. Merrifield. In such a synthesis, the peptide chain is normally attached by a benzyl-type carboxy-protective group to a polystyrene resin. A first amino acid is attached to the resin by a benzyl linkage, deblocked at its amino side, and coupled with a second amino acid, carrying a protected $\alpha$-amino group. The resulting protected dipeptide ester is deblocked with trifluoroacetic acid, converted into the free amine with base, and coupled to a second N-protected amino acid. After many repetitions of these steps, the complete peptide is cleaved from the resin with acid treatment. By using the insoluble resin support it is possible to isolate the product of each coupling reaction simply by filtering the resin and washing it free of by-products and excess starting materials. In fact, the synthetic processes are so simplified and the time required for one cycle is so shortened that in recent years it has become quite common to use automated peptide synthesizers. (See for example Barany, G. and Merrifield, R. B., "The Peptides, Vol. 2": Academic Press, Inc., New York, 1979, pp. 1–284; or Kemp-Vellaccio, "Organic Chemistry", pp. 1030–1032 (1980)).

Normally, the synthesis of peptides, either in solution or in solid phase, culminates in a final strong acid step in which all the protecting groups and the polymeric support are removed. For this purpose, acids with strong protonating properties such as hydrogen fluoride (Lenard, J. et al, Journal of the American Chemical Society, 89:181–182 (1967)), hydrogen bromide (Merrifield, R. B., Biochemistry, Vol. 3, 1385–1390 (1964)) or sulfonic acids (Yajima, H. et al, Chem. Pharm. Bull., 22:1087–1094 (1974)) have been used. However, several serious side reactions are known to be associated with these strong acids. For example, alkylation of nucleophilic side chains of tyrosine, methionine, tryptophan and cysteine, by carbocations generated from the alcohol component of the protecting groups (benzyl, tertiary butyl, and the like), is normally observed (See for example, Martinez, J. et al, Synthesis: 1981, 333–356). Another problem is dehydration of the protonated side chain carboxylic acid of aspartic and glutamic acids, followed by acylation reactions of the resulting acylium ions (Feinberg, R. S. and Merrifield, R. B., J. Amer. Chem. Soc. 97:3485–3494 (1975)). For example, the design of phenolic OH tyrosine protecting groups has been a challenging problem for peptide synthesis. The difficulty has been the tendency of the alkylation of the phenolic ring of tyrosine during strong acid removal of the O-alkyl-tyrosine protecting group. Among the commonly used protecting groups for tyrosine are R=benzyl, 2,6-dichlorobenzyl, 2-bromobenzoxycarbonyl and cyclohexyl. Of these, O-benzyl tyrosine gives the most alkylated product during strong acid treatment. This is shown in Scheme I:

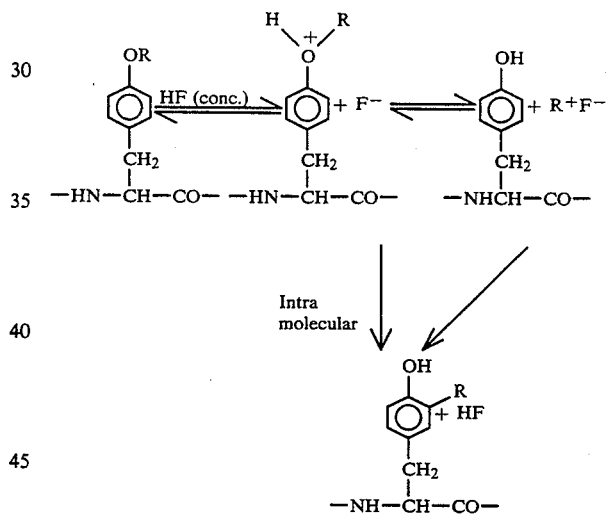

It has long been recognized that the 3-alkylated product (2) is the result of a cleavage mechanism in which the generated alkylcarbocation leads to the C-alkylation of the nucleophilic phenyl ring at the 3-position.

Sequential acid treatment during peptide synthesis, also often leads to electrophilic alkylation of unprotected tryptophan residues. This alkylation has been recognized to be more serious than the final strong acid cleavage step (Chino N. et al, Peptide Chemistry 1977 Protein Research Foundation, pp 27–32, Osaka, Japan). For example, the acidolytic removal of $N^\alpha$-tertbutoxycarbonyl group by trifluoroacetic acid results in about 30% of t-butylated tryptophan side products. Although the seriousness of the alkylation can be reduced in the presence of appropriate scavengers during the acid treatment, it is best to prevent the alkylation side reaction by protecting the indole moiety against electrophiles during the synthesis. This has been achieved by using $N^i$-formyl protecting groups, which effectively decrease the electrophilicity of the indole tryptophan ring and prevent alkylation side reactions. N$^i$-formyl tryptophan is stable to strong acid, including HF and sulfonic acids, but is usually removed after the strong acid deprotection of side chain protecting groups and removal from the resin support, by nucleophiles or aqueous bases, thus requiring an additional step, and resulting in further side reactions.

Still another amino acid residue which is the subject of problems during peptide synthesis is methionine. The incorporation of unprotected methionine into a synthesis faces side reactions of the thioether side chain being S-alkylated to sulfonium, or oxidized to sulfoxide groups. Since this side reaction is often left to be corrected during the purification step, not all S-alkylation is reversible (see for example Hofmann, K., Journal of the American Chemical Society 87: 631 (1965)). Alternatively, the use of methionine sulfoxide (met (O)) in the synthesis avoids the S-alkylation side reaction due to reduced nucleophilicity of the thioether side chain. However, both strategies result in the similar uncertainty of converting met(O) to met at the purification step. In general, methionine sulfoxide is stable to HF cleavage conditions and requires subsequent thiolytic reductions to methionine, after the removal of all the protecting groups. This again necessitates an extra step, and is, in addition, always slow, and often accompanied by side reactions (Houghton, R. A. Analytical Biochemistry 98: 36 (1979)).

The art has, for a long time, sought final step deprotection conditions which will overcome one or more, or possibly all, of the aforementioned problems. Thus, several studies on the effect of nucleophilic sulfur scavenger systems during acidolytic deprotection have appeared in the literature on peptide chemistry. In 1977 it was observed by Brady et al (Journal of Organic Chemistry 42: 143 (1977)) that dimethyl sulfide enhanced the rate of cleavage of the benzoxycarbonyl group ("Z group") in trifluoroacetic acid. Kiso et al (Chem Pharm Bull 28: 673 (1980)) found that the Z group could be completely removed by trifluoroacetic acid at room temperature when thioanisole, instead of anisole, was employed as a cation scavenger. These authors also stated that removal of the benzyl group (Bzl) from Tyr(Bzl), Thr(Bzl) and Ser(Bzl) by trifluoroacetic acid was accelerated by various sulfur compounds, but to a different extent. Yajima et al (Chem Pharm Bull 28: 1214–1218 (1980)) developed a system of using trifluoroacetic acid-thioanisole-m-cresol for the removal of benzyloxycarbonyl groups from N-ω-amino group of lysine. Kiso et al (Chem Pharm Bull 26: 2563–2564 (1978)) described the use of thioanisole as a scavenger for the deprotection of O-protected tyrosine under acidic conditions. Mixtures of anisole and HF were also tested in their work and the extent of rearrangement of tyrosine protected with 2,6-dichlorobenzyl, or tyrosine protected with benzyl, were examined. Finally, Node et al have suggested the use of mixtures of dimethylsulfide and aluminum trichloride for dealkylation of esters, such as aliphatic or aromatic carboxylic acid esters.

All of the aforementioned research, however, is based on the use of acids such as HF or trifluoroacetic (TFA) in high concentrations (>60–65%). Under these conditions carbocations are generated due to an $S_N1$ type of mechanism, and scavengers are therefore necessary to remove these carbocations. In some instances it has been proven useful to work with an acid such as HBr which operates partly on a $S_N2$ mechanism, and may thus prevent side reactions (Homer, R. B. et al Proc. Chem. Soc., 1963, 367). Hydrogen fluoride, however, which is nonoxidizing and much more volatile, is usually much preferred over HBr. No successful method using HF, which prevents the serious side reactions described previously, has yet been designed by the art.

A need therefore continues to exist for a deprotection reagent for peptide synthesis, especially for solid phase peptide synthesis, which will not suffer from the severe side reactions, rearrangements, and the like which characterize the reagents of the prior art, and which may also serve as a deprotection reagent for a variety of amino acid residues.

SUMMARY OF THE INVENTION

It is therefore an object of the invention to provide new reagents for acidolytic deprotection of amino acid residues in peptide synthesis.

It is another object of the invention to provide a method for the synthesis of peptides.

These and other objects of the invention as will hereinafter become more readily apparent have been attained by providing:

A method of releasing a functional group present in an amino acid or amino acyl residue from a resin or protecting residue which is bonded to said functional group by a linkage having proton affinity, which comprises:

reacting said functional group bonded to said resin or protecting residue with a mixture of HF and a base, for a time and under conditions effective to produce said release;

wherein the amounts of HF and base in said mixture are adjusted so as to cause said release to occur substantially by an $S_N2$ mechanism.

Another object of the invention has been attained by providing:

In a method of synthesizing peptides which includes protecting amino acid or amino acyl side residues with acid labile protecting groups through a linkage having proton affinity, the improvement wherein said protecting groups are removed with a mixture of HF and a base, wherein the amounts of HF and base in the mixture are adjusted so as to cause the removal of said protecting group to occur substantially by an $S_N2$ mechanism.

Yet another object of the invention has been attained by providing:

In a method of synthesizing peptides by the solid-phase methodology, wherein the growing peptide chain is covalently attached by a functional group through a linkage having proton affinity, to the organic residue of an insoluble resin, the improvement wherein said peptide is detached from said resin using a mixture of HF and a base, wherein the amounts of HF and base in said mixture are adjusted so that said detachment occurs substantially by an $S_N2$ mechanism.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 9A demonstrates the high pressure liquid chromatographic analysis of crude Cecropin A(1-33) on a reverse phase μBondapak C-18 column (4×300 mm), linear gradient of 10 to 50% solution B ($H_2O:CH_3CN:H_3PO_4$ 2:8:0.01, v/v/v) into solution A ($H_2O:CH_3CN:H_3PO_4$ 9:1:0.01, v/v/v), 2 ml/min. Detection at 225 nm, 0.1 absorbance full scale;

FIG. 9B demonstrates the high pressure liquid chromatographic analysis of purified Cecropin A(1-33) on a reverse phase μBondapak C-18 column (4×300 mm). Conditions of the analysis are similar to those in FIG. 9A;

FIG. 10 demonstrates the high pressure liquid chromatographic analysis of crude (Tyr[22]) glucagon on a reverse phase μBondapak C-18 column (4×300 mm), linear gradient of 30 to 50% solution B ($H_2O:CH_3CN:H_3PO_4$ 2:8:0.01, v/v/v) into Solution A ($H_2O:CH_3CN:H_3PO_4$ 9:1:0.01, v/v/v), 2 ml/min, Detection at 280 nm, 0.1 absorbance full scale;

DESCRIPTION OF THE PREFERRED EMBODIMENTS

Figure 1:
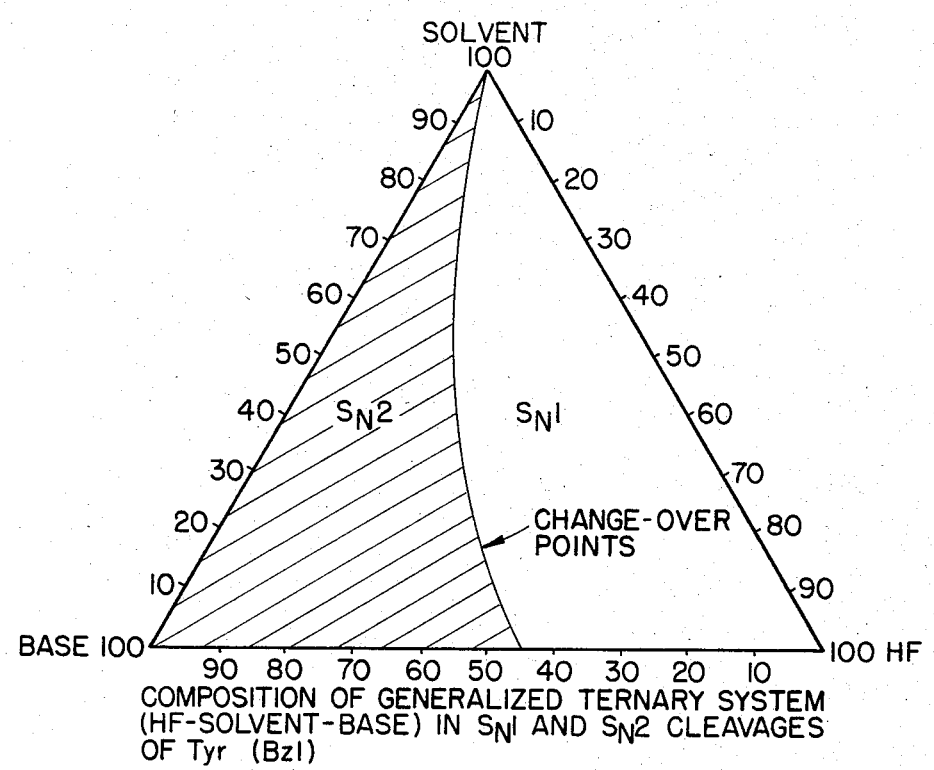
FIG. 1 demonstrates the composition of a generalized ternary system (HF-solvent-base) in the $S_N1$ and $S_N2$ cleavages of Tyr(Bzl). The shaded area is of the $S_N2$ type. The smooth curve dividing the equilateral triangle is made up of points where transition from $S_N2$ to $S_N1$ is observed.

In their search for a reagent which would be useful for carrying out the final step in peptide synthesis, (i.e., the deprotection of all amino acid functional groups which are protected with acid labile protecting groups, and, when working in solid phase, the detachment of the synthetic peptide from the solid phase), the present inventors discovered limiting conditions within which HF could be used substantially without any of the serious side reactions of the prior art, and could be used for an expanded number of deprotections. Although in the prior art it has generally been believed that HF is, in fact, useful as a final step reagent in peptide synthesis, the prior art has had to accept the fact that severe side reactions occur with this reagent. The present inventors, however, have discovered that, under certain controlled circumstances, HF can be used without the side reactions.

The controlled circumstances or limiting conditions for final step reaction, according to the present invention, are those wherein HF is used at much lower concentrations than was previously customary in the prior art. In addition, the reaction is carried out in the presence of a base. The amount of HF is adjusted in the reagent mixture so that it will be sufficient to at least partially protonate the linkage joining the functional group present in the amino acid or amino acyl residue with the residue to be cleaved therefrom, yet insufficient to fully protonate the base present in the mixture.

Without being bound by any particular theory, applicants believe that, under these conditions, the fraction of unprotonated base present in the mixture enters—as a nucleophile—into a bimolecular nucleophilic substitution reaction ($S_N2$) with the detachable organic residue involved, (e.g. the protecting group), thereby releasing the amino acid or amino acyl functional group in protonated form. In other words, applicants have found conditions wherein an HF-based, final step reagent is fully capable of utilizing an $S_N2$ type of mechanism, instead of the $S_N1$ cleavage mechanism seen in the prior art. The first of these two alternatives is schematically shown in Scheme II:

Scheme II ($S_N2$ mechanism):

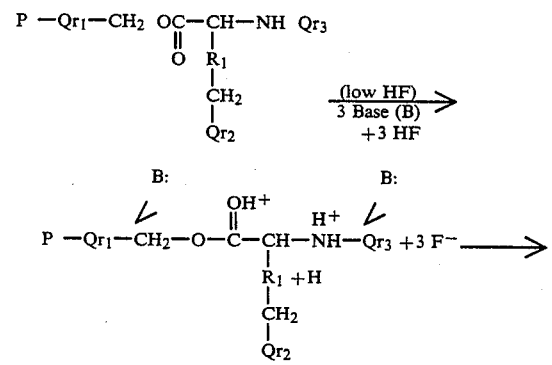

-continued

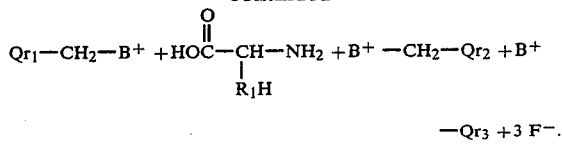

$$-Q_{r3} + 3F^-.$$

In this scheme, P is an insoluble polymeric resin used in solid phase synthesis. $-Q_{r1}-CH_2-$, $-Q_{r2}-CH_2-$ and $-Q_{r3}$ are organic residues which are released from the amino acid functional groups during the reaction. Thus, $-Q_{r1}-CH_2-$ is attached to the polymeric resin and serves as the bridging group between the polymeric resin and the peptide (in this case a single amino acid, shown for illustration only). $Q_{r2}-CH_2-$ is an organic residue which is utilized as a protecting group for the amino acid functional group $R_1$. $Q_{r3}$ is a protecting group for the terminal amino group. B is a base. Scheme II shows the probable mechanism by which reactions occur in the present invention. First, protonation occurs at the residue $R_1$ having proton affinity, and at the carbonyl oxygen of the terminal carboxy group of the amino acid. In a second step, the base attacks the $CH_2$ carbon of the organic residue, releasing the protonated functional groups, and yielding detached and deprotected amino acid, as well as resin, and protecting groups covalently attached to the base.

In comparison, at high concentrations of hydrogen fluoride, such as those of the prior art, it is believed that the mechanism is as shown in Scheme III.

Scheme III ($S_N1$ mechanism):

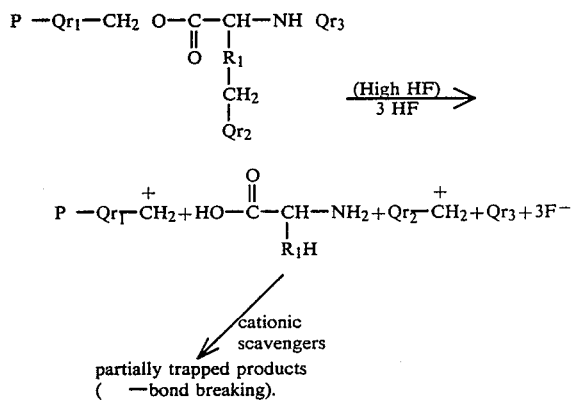

partially trapped products
( —bond breaking).

It is shown in Scheme III that, at high HF concentration, the mechanism proceeds via free carbocations $P-Q_{r1}-CH_2^+$, $Q_{r2}-CH_2^+$ and $Q_{r3}^+$. In the prior art, these carbocations have been scavenged with cationic scavengers such as bases. However, in the present invention, the primary function of the base is to serve as the nucleophilic displacement reagent, although it is envisioned that some cationic scavenging would also occur by such base. Because of the nature of the mechanism, and the absence of free cationic intermediates (which would otherwise undergo acylation or alkylation reactions), such side reactions are severely suppressed in the present invention.

In essence, the invention is based on the discovery that a changeover in mechanism from $S_N1$ to $S_N2$ occurs in going from high HF concentrations to low HF concentrations. Although such change in mechanistic behavior has been observed with other acids (see for example Yates, K. and McClelland, R. A. Journal of the American Chemical Society 89: 2686–2692, 1967), the present inventors were the first ones to recognize the existence of such changeover in HF solutions, and to successfully utilize this changeover in formulating a reagent for final-step reaction in peptide synthesis.

A great variety of functional groups present in amino acids or amino acid residues can be involved in deprotection reactions. In addition, the term "functional group" as used in the present invention and claims also includes the amino acid group utilized to bind the peptide chain to a solid polymeric resin, in the case of solid phase synthesis. Normally, this bridging functional group is a carboxy group. The most common functional groups which are protected during peptide syntheses are those present in the side chains of the amino acids, and include such functional groups as OH (both aromatic and aliphatic); $NH_2$; COOH; nitrogen atoms of imidazole rings, of tryptophan rings, or of arginine; and SH or $-S-CH_3$. When one includes the resin-bridging amino acid functional group used during solid phase synthesis, the amino acids involved in the method of the present invention thus comprise the aliphatic amino acids, such as glycine, alanine, valine, leucine, and isoleucine; the hydroxy amino acids such as serine and threonine; the dicarboxylic amino acids and amides such as aspartic acid, asparagine, glutamic acid and glutamine; the amino acids having basic functions such as lysine, hydroxylysine, histidine, and arginine; the aromatic amino acids such as phenylalanine, tyrosine, tryptophan, and thyroxine; the sulfur containing amino acids such as cysteine and methionine; and other amino acids such as proline or hydroxyproline. Any other amino acids, natural or non-natural, are of course also included in the present invention. The amino acids may be present by themselves, at the end, or along the chain of a synthetic peptide.

By the term "releasing" as used in the invention and in the claims is meant the splitting or cleavage of the covalent chemical bond which serves to unite the amino acid functional groups to their respective protecting groups or resin-bridging residues. In the process of the present invention, i.e. in the final step of peptide synthesis, the functional groups are freed from whatever protecting group or resin they may have been covalently attached to during the previous process of synthesis.

The terms "resin or protecting residue" as used in the present invention and in the claims are meant to include both the normally used protecting groups, as well as the organic functional groups which link a growing peptide chain to a polymeric resin. In the most general sense, these residues should be able to undergo bimolecular nucleophilic substitution by a base, i.e. they are the electrophilic acceptors in the $S_N2$ mechanism. A wide range of protecting residues are used and are well known to the art. They include for example, benzyl, 2-chlorobenzyl, 2,6-dichlorobenzyl, bromobenzyl, carbobenzoxy, methylbenzyl, methoxybenzyl, benzhydryl, substituted carbobenzoxy, and the like. In the case where the residue is a bridging residue between the peptide and a polymeric resin, it has been customary to use the benzyl group in that role, since it is derived from attachment of the first amino acid in the peptide to chloromethylated residues on a polystyrene resin. The invention, however, is not only limited to that particular embodiment. Polyacrylamide, substituted polyethylenes, polyethyleneglycol, phenolic resins, polysaccharides (e.g. Sephadex, cellulose) soluble, non-crosslinked polystyrene, etc. can also be used as resins.

The linkage linking the functional group and the resin or protecting residue is, by the nature of the atoms present therein (O, N or S in most cases) basic, that is, it has proton affinity.

Any bond cleavable by a bimolecular nucleophilic substitution reaction of the base on the protecting or resin residue can be used. Preferably, the bonds are acidolytically labile, and include all those which, in the past, have been deprotected with mixtures containing high concentrations of HF. The most common linkages as used in the invention are ethers or thioethers ($R^1$—$CH_2$—O (or S) —$CH_2$—$R^2$), esters

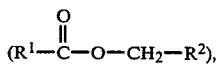

carbamates

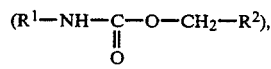

benzhydrylamide, sulfenylamine, or sulfonylamides, wherein $R^1$ is the radical of an amino acid or aminoacyl moiety and $R^2$ is the radical of a protecting group therefor, or $R^2$ is a polymeric resin. In the most preferred mode, $R^2$ is a phenyl or halo-substituted phenyl group which may or may not be attached to a resin.

The bases useful in the present invention are normally weak bases since, given their crucial role as nucleophiles in the reaction, they have to comply with the condition that they not be fully protonated by the HF. The most preferred bases are those having $pK_a$ values ranging between −2 and −11. In addition, the bases should be nucleophilic. Among the preferred bases are sulfur containing bases, such as thiols or sulfides. Among the best are di-$C_1$-$C_{10}$-alkylsulfides (linear or cyclic) wherein the alkyls are the same or different, alkyl phenyl sulfides, thiophenols, p-thiocresol, 3,4-dithiotoluene, 1,2-dithioethane, ethanethiol, thioanisole, tetrahydrothiophene and the like. Oxygen bases such as phenol, m-cresol, p-cresol or anisole can also be used. Because of their nucleophilicity, pKa and volatility properties, the di-lower alkyl sulfides are the most preferred and dimethylsulfide is, at the present time, the best of all.

The concentration of HF is to be adjusted according to the proton affinity (strength) of the accompanying base and according to the proton affinity of the linkage between the functional group and the protecting or resin residue, in order to cause the mechanism to be predominantly $S_N2$ in character, rather than $S_N1$ in character, i.e., fall within the range wherein the linkage is partially protonated and the base is not fully protonated. Given the availability of "indicator systems," see infra and of pKa values for bases and proton affinity values of the linkage functional groups, e.g. ethers, thioethers, carbamates, amides, acyl guanidine, acylimidazole and the like, it is a matter of testing or calculation to define this concentration. The concentration will also depend on the polarity of the solvent mixture, the hydrogen-bonding ability of the cosolvent and the dissociation of HF itself. Therefore, in the more polar solvents the effective HF concentrations may be smaller than in less polar solvents. In general, the concentration of HF is adjusted so that the acidity of the solution, as measured by the Hammett acidity function HO (see for example Hammett, Chemical Reviews 16: 67 (1935); "Physical Organic Chemistry" McGraw-Hill Book Company, New York, N.Y. 1940; as well as Hyman and Garber "The Hammett Acidity Function Ho for Trifluoroacetic Acid Solutions of Sulfuric and Hydrofluoric Acids," Journal of the American Chemical Society, Volume 81, 1847, 1849 (1959), both of which are herein incorporated by reference), is at most within plus or minus one whole logarithmic unit of the pKa of the base. Thus, the acidity of the mixture may be in the range of from −1 to −11. In general terms, the percent by volume of HF in the solution can be between 0.1% and 60%. More particularly, in using lower dialkyl sulfides as the bases and as the diluents, the concentration of HF may range from about 15% to 50%, most preferably 20–40%.

In order for the method of the invention to proceed effectively, the linkage between the functional group and the protecting or resin residue has to be at least partially protonated. By "partially protonated" is meant that at least 1% of the linkage is in the protonated form and 99% is in the unprotonated form. This ratio can be calculated from the proton affinity of the linkage functional group. Also, the base should be sufficiently unprotonated. By the terms "sufficiently unprotonated" is meant that at least 1% should not be protonated and be free to function as a nucleophile.

The release reaction carried out in the final step of peptide synthesis according to the present invention can be performed over a wide range of temperature and time conditions, which conditions are only limited by experimental expediency and can be readily determined by those of ordinary skill in the art without undue experimentation. Normally, the reaction can be carried out at from about −10° C. to room temperature (∼25° C.), preferably at 0° C. The time can be ascertained by following the yield of free peptide, and is normally within the range of from 5 minutes to 12 hours. The reagent of the present invention is used in molar excess over the molar amount of protected and attached functional groups in the peptide.

The reagent can be used as such (HF plus base, binary systems) or diluted in a solvent, preferably in polar protic solvents such as trifluoroacetic acid, acetic acid, and other protic acids (ternary systems). The reagent can also be used in the presence of additional cationic scavenging compounds such as 1–20% v/v of phenols, indoles, ethers, thioethers, thiophenols, sulfides. Sufficient amounts of resin swelling compounds preferably 1–50%, especially 1–20%, of compounds such as aromatics, chlorinated hydrocarbons, ethers, esters and the like can also be added.

In the present invention the question of whether any given cleavage reaction is occurring under $S_N2$ or $S_N1$ mechanism conditions, can be readily determined (infra). The reaction can then be done under HF, solvent and base conditions which will fall within the (desired) $S_N2$ region.

The change-over point can be readily measured by a number of reactions ("indicator systems"). Some "indicator systems" that show the change of $S_N2$ to $S_N1$ mechanism are:

(a) Deprotection of Boc-Tyr(Bzl). (See Example 2 and FIG. 5). The $S_N2$ reaction in this indicator system is characterized (at 0° C., 1 hour) by a reduction in side product, 3-benzyl-tyrosine, and a corresponding quantitative increase in production of sulfonium salts. The $S_N1$ reaction, on the other hand, gives significant amounts of 3-benzyl-tyrosine as side product and, furthermore, it produces little sulfonium salts, but significant amounts of aromatic side products, due to the dimerization or polymerization of the benzylic cation. This pattern is repeatedly seen when such reaction product mixtures are analyzed by reverse phase high performance liquid chromatography.

Any system (binary or ternary or higher) wherein the amount of 3-benzyltyrosine is lower than about 15%, preferably lower than about 5%, and/or wherein the amount of sulfonium salts is higher than about 85%, preferably higher than about 95% in this indicator system, can be considered to be in the $S_N2$ region.

(b) Rate of deprotection of Ser(Bzl). The $S_N2$ reaction in this indicator system (at 0° C.) is characterized by a slow rate of benzyl protection group removal and a slow change in rate with the addition of HF, while the $S_N1$ reaction produces faster rate changes with the addition of HF. The slope change for the rate of reaction by the $S_N2$ mechanism is less than 1, while the slope change for the $S_N1$ type is greater than +2;

(c) In addition, the $S_N2$ type of reaction causes a chemical reduction of Met(O) to Met in the presence of the appropriate sulfide, and deprotects Trp(For) to Trp in the presence of a thiol. Both of these reactions are slow or do not occur significantly in an $S_N1$ type of reaction.

Therefore using any of these "indicator systems" (a, b or c) one skilled in the art can determine the changeover for any HF/base system, whether the system is binary or higher.

In binary HF/base mixtures, with phenolic or thiophenolic additives, there are many combinations that will be effective in the present invention, where the cleavage mechanism is largely an $S_N2$ type (as long as the sulfide is not totally protonated). For example, in systems with HF-sulfide as the binary mixture, the change-over of mechanism from $S_N2$ to $S_N1$ with respect to HF concentration (in vol %) is about 55% for dimethylsulfide, and about 65% for thioanisole. However, the addition of phenolic and thiophenolic compounds affects this change-over point. The effect depends on the solvent system. In general, the pKa of the weak base, such as sulfide, and the potentiating or deactivating effect of the added solvent will shift the change-over point. Usually, the weaker the base, the higher the concentration of the HF required for the change-over in mechanism. If thioanisole is further substituted with electron withdrawing groups such as Cl, Br, $NO_2$ etc., the pKa of the sulfide will be lower. Accordingly, the change-over point will be moved towards higher concentrations of HF.

Since the ability of the reagent of the invention to remove protecting groups or resin groups by an $S_N2$ mechanism depends on the $H_o$ of the acid system, it is possible either to potentiate or to deactivate the HF by the addition of various solvents. For example, trifluoroacetic acid (TFA) has long been known to potentiate the $H_o$ of HF. The $H_o$ value for 100% HF is $-11$ and for 50% HF in an inert diluent is $-6$. 100% TFA has a pKa of $-3.3$. However, the addition of 0.9% vol % of HF to TFA will bring the $H_o$ of the HF-TFA mixture to $-6.0$. Thus, when various concentrations of HF in TFA, containing 10% of dimethylsulfide, are used to test the change-over point from an $S_N2$ to an $S_N1$ reaction according to the tyrosine alkylation indicator system, it is found that the mechanism changes at only about 5% by volume of HF. This is in sharp contrast to the HF-dimethylsulfide binary system where the change-over point is at about 55% by volume.

Figure 2:
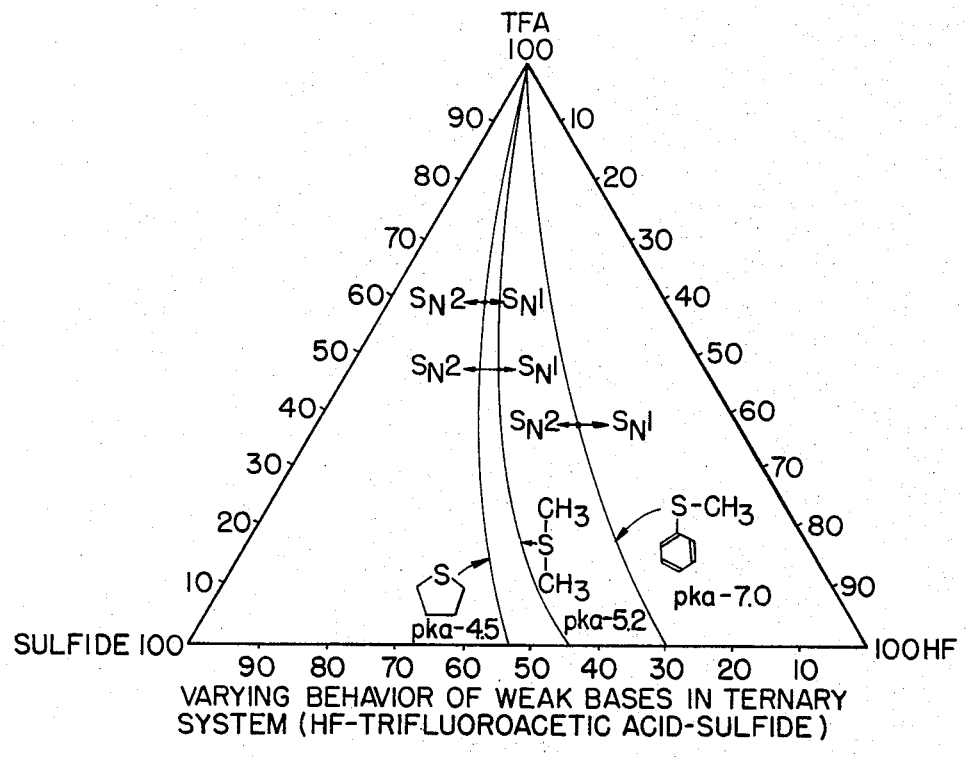
FIG. 2 demonstrates the different behavior of weak bases such as sulfides in a ternary system (HF-trifluoroacetic acid-sulfide) as represented by the equilateral triangle diagram. The smooth curves dividing the triangle show the change-over points from $S_N2$ to $S_N1$ mechanism when a given sulfide is used as base.
Figure 3:
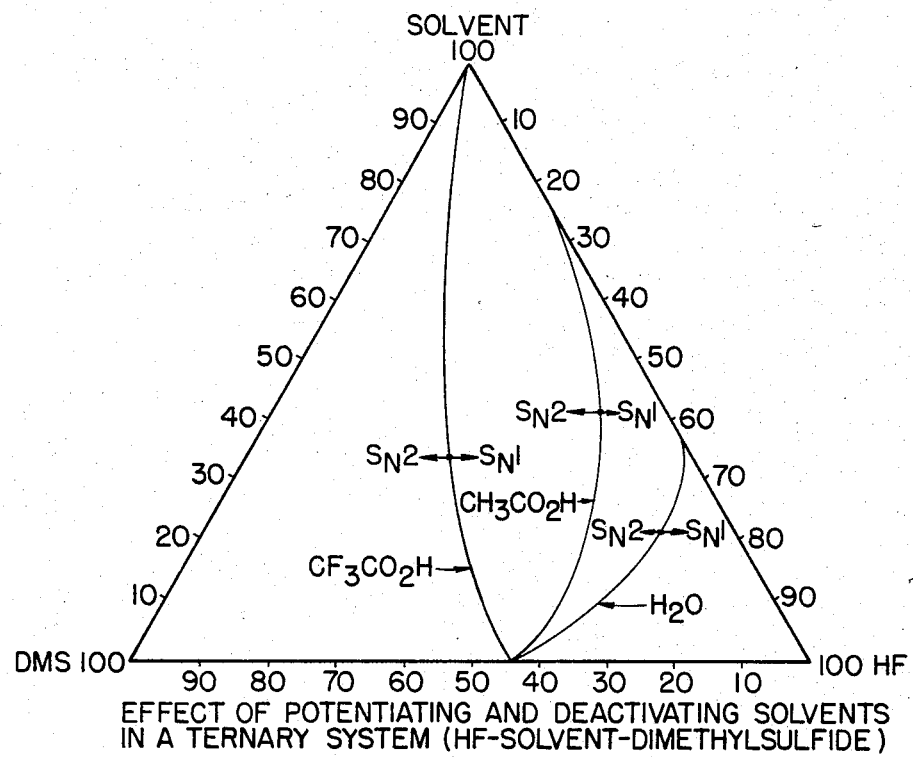
FIG. 3 demonstrates the effect of potentiating and deactivating solvents in a ternary system: HF-solvent-dimethylsulfide as represented by the equilateral triangle diagram.

The variation in the change-over point of a three-component system with changes in the composition can be conveniently represented on an equilateral triangle graph. FIGS. 1–3 illustrate the application of the invention results on a series of equilateral triangle plots. The three illustrated components e.g. solvent, HF and base occupy the apices of the triangle, which represent 100% of each component. Any point along the line opposite to the apex represents 0% of that component. The composition of any point in the system can be represented by the length of a perpendicular to the given side for each component. If the change-over points from $S_N2$ to $S_N1$ reaction given by the solvent, HF and base system are plotted as in FIG. 1, then a smooth curve can be drawn through these points, dividing the equilateral triangle into two parts. The shaded area represents the compositions of solvent, HF and base that operate through an $S_N2$ mechanism, while the clear part represents the compositions where the ternary mixture operates predominately through an $S_N1$ mechanism. The $S_N2$ area can be roughly divided into 3 regions. In part A, where the concentration of solvent is high ($>65\%$), the HF concentration is rather low ($<20\%$) and can still maintain an $S_N2$ character. In part B where the concentration of solvent is intermediate (30 to 65%) the HF concentration changes accordingly so as to give both an ionic and acidic condition. In part C, where the solvent concentration is low and the base increases $>35\%$, the HF concentration has to change to accomodate for the solvent change. Thus, in the final analysis, the HF concentration in such system can vary from 0.1 to 60% and still be effective as the deprotecting reagent.

When trifluoroacetic acid, HF and thioanisole (pKa—7) are plotted in the diagram, the $S_N2$ area becomes larger than the corresponding system where dimethylsulfide (pKa—5) is used (FIG. 2). This clearly reflects that thioanisole is a weaker base than dimethylsulfide and requires a stronger HF-TFA acid system to tie up all the sulfide and cause the change from an $S_N2$ to an $S_N1$ mechanism.

In practice there are many solvent systems that can potentiate the acidity function of HF and produce the just described effects. Solvents such as formic, acetic and other $C_1$–$C_{10}$ branched or unbranched aliphatic acids are common solvents in peptide synthesis, and can be used accordingly to substitute for trifluoroacetic acid.

A ternary system has an advantage over the HF-sulfide binary system in that it does not necessarily require a complicated HF apparatus. To achieve the effect of an $S_N2$ deprotection reagent, a stable HF-DMS (1:1 v/v) reagent can simply be diluted according to a three-component diagram with trifluoroacetic acid and additional sulfide, and used accordingly in plasticware. (An example of a two component system that does not require an HF apparatus is known, although it has several deficiencies and has not been used with a potentiating third component. Thus, an HF-pyridine complex (3:1, v/v) can be obtained commercially (Aldrich Chemical Co) as a stable compound, and can be diluted with TFA and sulfide to obtain a cleavage reagent within this invention.)

Solvent systems that form strong hydrogen bonds with HF will also deactivate and reduce the $H_o$ of HF.

Thus the change-over point of the $S_N2$ to $S_N1$ mechanism will be shifted toward higher concentrations of HF. Solvents such as $H_2O$, alcohols, phenols, thiols, or thiophenols fall into this category. An example of this system is represented in FIG. 3 in which HF, $H_2O$ and dimethylsulfide are plotted on the equilateral diagram. Since an addition of 10% of $H_2O$ will lower the $H_o$ to $-8.10$, the effect of even small amounts of $H_2O$ will be large. Accordingly the diagram in FIG. 3 shows a large area where the $S_N2$ mechanism predominates.

Finally, addition of certain salts can also affect the $H_o$ of HF. For example, the presence of Lewis acids such as $BF_3$, $SbF_5$, or $TaF_5$ raises the $H_o$ of HF to so called "super acid" strength, i.e. $H_o < -11$. Thus, in such mixtures as $HF-BF_3-DMS$ or $HF-BF_3-TFA-DMS$ the mechanism change-over will be shifted to a much lower concentration of HF. On the other hand, addition of NaF, KF of LiF will change the $H_o$ of HF to a more positive value, making it a weaker acid system. In such system of HF-KF-DMS, or HF-KF-DMS-TFA, the change over point will shift to a higher concentration of HF.

In addition to being useful for the deprotection of acid labile protecting groups of such functional groups as carboxylic or hydroxy groups, it has been discovered that the final step reagent of the present invention is also capable of deprotecting formylated tryptophan (Trp(For)) in one single manipulation. In this particular embodiment, it is preferred to add between 1 and 10% by volume of a $C_1-C_{10}$ alkylthiol or arylthiol scavenger to the low HF concentration reagent, wherein aryl can be phenyl or lower alkyl- or halo substituted phenyl. Side products which are observed in high concentration HF/thiol mixtures are not found at low HF concentrations. These by-products are thiol addition side reactions to Trp(For), and occur in high concentrations of HF. Other scavengers can of course also be used, such as phenols, substituted phenols and the like, in addition to the HF/base/thiol mixture. It is believed that a low HF-base-thiol condition, where the HF concentration is maintained within the limitations described previously, is optimal. When HF concentrations are above or below these limits, deprotection of the formyl groups is either too slow or side reactions occur. If a weaker acid such as trifluoroacetic acid is substituted for HF at the same concentration, the deprotection of formyl tryptophan is found to be too slow (t ½ greater than 24 hours).

Another discovery made by the present inventors is that when the accompanying base in the low HF reagent in the present invention is a reductant, capable of reducing a sulfoxide group, the reagent is fully capable of reducing methionine sulfoxide to methionine. Thus, for example, when methionine sulfoxide is treated with HF and a dialkysulfide as the base, reduction is essentially quantitative.

Given these results, the reagent of the present invention can be used in one step to mildly and without side reactions deprotect most functional groups present in peptides in the final step, detach the peptide from the polymeric resin, remove formyl groups from tryptophan residues and reduce methionine sulfoxide to methionine.

The regeant can also be used in multi step deprotection procedures, wherein the first step is deprotection/-detachment with the reagent of the peptide synthesis and, of course, the most commonly utilized, solid phase peptide synthesis, most especially in the automated solid phase peptide synthesis. Thus, the reagent can be provided pre-made for direct utilization in plastic vessels or in automated peptide synthesizers.

In this respect, compositions which are useful for the methodology of the present invention are also covered by the present application. These compositions encompass those comprising HF solutions plus $C_1-C_{10}$ dialkyl sulfide or alkyl phenyl sulfide, especially dimethysulfide, wherein the amounts of HF and sulfide are adjusted so that when said reagent is used with any of the "indicator systems", supra, the reagent will result in the operation of an $S_N2$ mechanism. The compositions can be binary, ternary or higher and contain solvents, scavengers, swelling compounds, etc.

Having now generally described this invention, the same will be better understood by reference to certain specific examples, which are included herein for purposes of illustration only and are not intended to be limiting unless otherwise specified.

EXAMPLE 1

Deprotection of Ser(Bzl).

Figure 4:
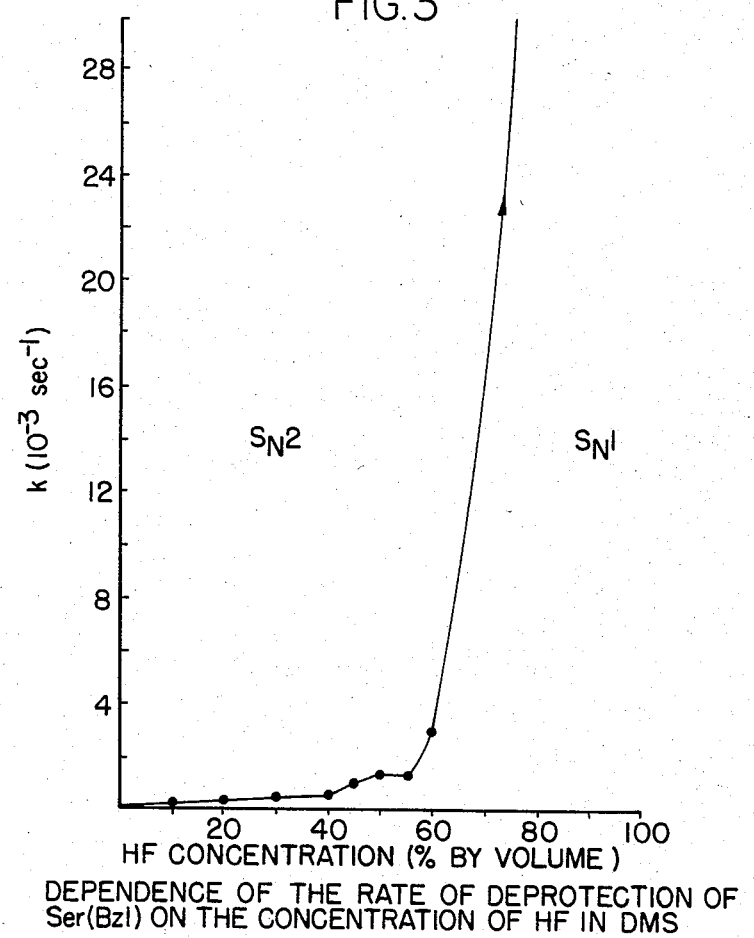
FIG. 4 demonstrates the dependence of the rate of deprotection of Ser(Bzl) on the concentration of HF in dimethylsulfide.

The kinetic response for the deprotection of Ser(Bzl) to changes in acidity of HF and dimethysulfide (DMS) was studied. (This is one of the so called "indicator systems", supra). The deprotection mechanism of HF-DMS mixtures can basically be accommodated by two distinct acid-rate profiles (see FIG. 4). At high HF concentration (greater than 50% of HF) the rate of removal of Ser(Bzl) increased rapidly with rising concentration of HF. The rate of deprotection of Ser(Bzl) at 50% HF concentration was found to be $1.35 \times 10^{-3} sec^{-1}$ but increased to $3.01 \times 10^{-3} sec^{-1}$ at 60%. The rate was too fast to be measured accurately in concentrations above 60% but was estimated to be $23.0 \times 10^{-3} sec^{-1}$ at 75%, and $60.0 \times 10^{-3} sec^{-1}$ at 90% HF. Thus, for practical purposes, most Ser(Bzl) residues were deprotected at 0° C. in the first two minutes when exposed to the high concentration of HF used in normal deprotecting procedures. However, when the HF concentration was below 50%, the rate of change was much less dramatic and slower. With a slope of 0.13 the rate increased only 3-fold from 10% to 40% of HF concentration. For the same amount of increase of HF concentration from 60% to 90% of HF, the increase was over one 20-fold with a slope of 2. Such a sudden break in the rate-acidity profile is indicative of a change-over from an $S_N2$ to an $S_N1$ mechanism, as is shown in FIG. 4. The role of dimethylsulfide in this example serves not only as diluent but also as nucleophile. Thus, the HF-dimethylsulfide binary mixture resembles a nucleophilic acid such as HBr, which is known to remove $N\alpha$- benzoxycarbonyl protecting groups by an $S_N2$ mechanism, rather than by an $S_N1$ mechanism in sulfuric acid (Homer, R. B. et al Proceedings of the Chemical Society 1963, 367).

The change-over in mechanisms of HF-dimethylsulfide can also be explained by the acidity function of HF-dimethylsulfide mixtures at various concentrations. Since dimethylsulfide has a pKa of $-5.3$, the effective acidity function for this binary mixture should be near the pKa of dimethylsulfide so that it is still largely unprotonated and available for the nucleophilic participation of the bimolecular nucleophilic reaction mechanism. It has been found that at 25% by volume of HF and dimethylsulfide, the Ho of the solution as measured by Hammett indicator is between $-4.6$ and $-5.2$. Furthermore, at this range of acidity function, most protecting groups such as esters, ethers and carbamates are also protonated. As the HF concentration increases, the acidity function also increases, and at 90% HF the Ho was found to be between −8.2 and −9.1, a concentration at which dimethylsulfide becomes fully protonated. The reaction, in this range, falls within an $S_N1$ type of mechanism largely due to HF itself. At HF concentrations lower than 25% the Ho decreases to such extent that the solution gradually loses the protonating capacity required to remove these protecting groups.

It is clear from FIG. 4 that a wide range of HF concentrations below 50% in dimethylsulfide can be used to remove protecting groups and can still lie mainly within the $S_N2$ mechanism. In theory, the HF concentration should be kept as low as possible, although at low HF concentration, the protonating property of the mixture at 0° C. is decreased and requires a longer reaction time. Based on Hammett's indicator studies an approximately equimolar binary mixture of HF:dimethylsulfide (1:3 v/v) is satisfactory for most purposes. A mixture of HF and diethylsulfide (1:1 molar ratio) was found by Adam and Katz (Journal of Molecular Spectroscopy, Vol. 1: 336–332 (1967)), to be a loose complex, but diethylsulfide is not strongly protonated.

COMPARATIVE EXAMPLE 1

To test the efficacy of the new cleavage conditions, HF-dimethylsulfide (1:3, v/v) was compared with HF-anisole (9:1, v/v) as a deprotecting agent. Both remove benzyl alcohol-derived protecting groups efficiently in one hour as shown in Table I.

TABLE I

Deprotection of Side Chain Protecting Groups by High or Low Concentration of HF

| Amino Acid Derivative | Products (mole %) | |
|---|---|---|
| | High HF[1] HF:anisole (9:1, v/v) | Low HF[2] HF:DMS (1:3, v/v) |
| Boc—Lys(Z) | 100 | 100 |
| Boc—Ser(Bzl) | 100 | 100 |
| Boc—Glu(OBzl) | 87 (13)[3] | 100 |
| Boc—Tyr(Bzl) | 75 (25) | 99.5 (0.5) |
| Boc—Trp | 95 (5) | 100 |
| Boc—Met(O) | 0 (100)[4] | 100 |
| Boc—Arg(Tos) | 100 | <10 |
| Boc—Arg(NO2) | 100 | <5 |
| Boc—Cys(4-MeBzl) | 75 (25) | <10 |
| Boc—Asp(OcHex) | 100 | <5 |

[1]For 1 h at 0° C.
[2]For 2 h at 0° C.
[3]Side products are indicated by parenthesis
[4]As Met(O) starting material
Boc = butyloxycarbonyl; Bzl = Benzyl; Z = Benzyloxycarbonyl In addition, the HF/DMS reagent removed the sulfoxide from Boc-Met(O). Protecting groups which are known to be deprotected only by $S_N1$ are expected to be stable or to be removed very slowly. Thus, the low HF-dimethylsulfide mixture did not significantly deprotect Arg (Tos), Arg (NO2), Cys(4-MeBzl) or Asp(O-cHex), and only partially deprotected Tyr(2,6-Cl2-Bzl) (65% in two hours at 0° C.). The HF-dimethysulfide mixture was found to be a poor swelling solvent for the cleavage of peptide resins but could be improved by the addition of about 10% p-cresol. A mixture of HF-DMS-p-cresol (25:65:10, v/v) gave excellent results. Thus, for the cleavage of a very acid stable protecting group such as Arg(Tos) or peptidyl resins such as benzhydrylamine resins, a two stage low-high HF concentration cleavage method was instituted. The sample was treated first with low concentration HF-DMS-p-cresol for one or two hours at 0° C. to remove the carbocations by trapping as alkyl dimethylsulfonium salts. After evaporation of the HF and DMS, additional HF was added to the reaction vessel to give 80% HF, 20% p-cresol by volume, to allow the complete removal of other more acid-stable groups. The 80% HF and 20% p-cresol has been shown to be the optimal condition for the suppression of the dehydration of protonated glutamic acid side chains to the acylium ion, while removing the acid resistant groups. Furthermore, the advantage of the low concentration HF deprotecting procedure of the present invention is manifested in the minimization of several side reactions associated with the high HF anisole mixture (Table 1 supra). For example, Tyr (Bzl) which gave 20% of 3-alkytyrosine in high HF anisole (9:1) or high HF-DMS (9:1) mixture, provided less than 0.5% of alkylated product in the low HF-dimethylsulfide mixture, a greater than 40-fold improvement and a result comparable to the best HBr cleavage condition for Tyr (Bzl). Similarly, glutamic dehydration in the presence of aromatic scavengers, e.g. anisole, gave no aromatic ketonic adduct. All these are indicative that the cleavage at low concentration HF-dimethylsulfide is quite different than the high HF-anisole mixture.

EXAMPLE 2

Deprotection of Tyr(Bzl)

This is one of the "indicator systems" to determine whether reaction is $S_N2$ or $S_N1$, supra.

Figure 5:
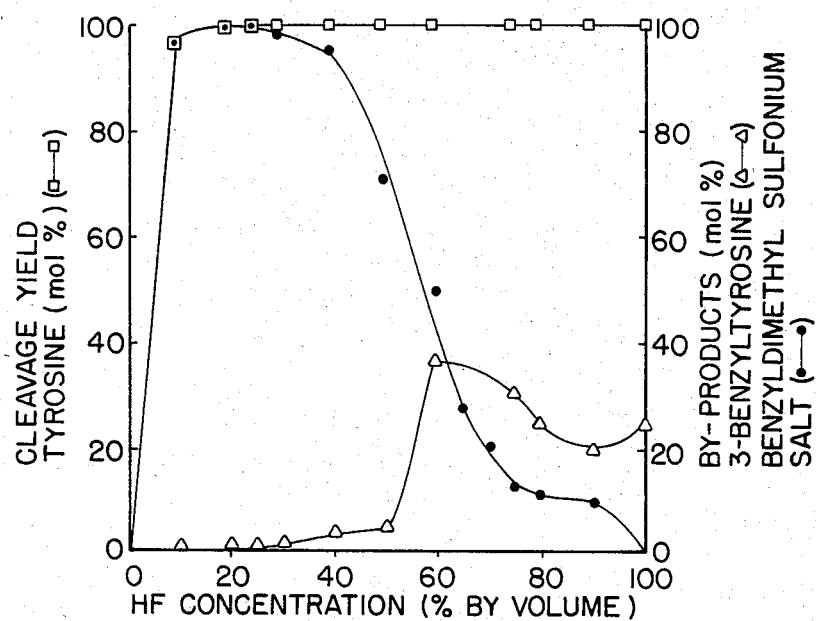
FIG. 5 demonstrates the dependence of deprotection of O-Benzyltyrosine on the concentration of HF in dimethylsulfide, showing both the cleavage yield of O-Benzyltyrosine (—□—), the formation of 3-Benzyltyrosine by the alkylation side reaction (—△—) and of the benzyldimethylsulfonium ion (—●—)

When Boc-Tyr(Bzl)-OH was treated at different concentrations of HF(10–100%) in dimethyl sulfide at 0° C. for one hour, the products, tyrosine and 3-benzyltyrosine, were analyzed and quantitated both by ion exchange chromatography and reverse phase HPLC to determine the mole percentage of the side reaction. As shown in FIG. 5, the cleavage of O-benzyltyrosine was near quantitative at 0° C. for one hour, when the HF concentration was above 10%. The amount of 3-benzyltyrosine increased very slowly at the low HF concentrations, but rose rapidly when HF concentrations were above 45%. Since, at high HF concentrations, the DMS is fully protonated, the cleavage of O-benzyl tyrosine was of the $S_N1$ type and was due to HF itself without participation of a nucleophile. The alkylated tyrosine product is derived from the free benzyl carbocation. When the HF concentration was between 20–40%, the amount of 3-alkylation product was found to be only 0.3–3% indicating that little benzyl carbocation was free and that the unprotonated dimethylsulfide acted as the nucleophile in the bimolecular cleavage mechanism to give benzyldimethylsulfonium fluoride. The extent of rearrangement of Tyr(Bzl) in HF-dimethysulfide mixtures was, therefore, very much dependent on the HF concentration. Matsuura, S. et. al. (1976) J. Chem. Soc., Chem. Commun. 451–452, have reported that HF-pyridine-anisole (14:6:2, v/v/v) in the cleavage of Tyr(Bzl) provides only 68% recovery yield of Tyr. Presumably the low yield is due to the 3-alkyltyrosine product. The amount of side product in 70% HF and DMS is found in the present invention to be about 38%. As HF concentration increases above 60%, the solution becomes more polar and favors a disassociation from the amino acid of the benzyl cation, which can then be captured by the scavengers. Thus, the more polar the HF scavenger system, the less will be the alkylation due to internal return of the carbonium ion. This effect can be observed by noting that at about 90% HF, the alkylation product formed to the extent of 27% in dimethylsulfide, 25% in anisole, 9% in p-cresol and 6% in thioanisole showing p-cresol and thioanisole to be the best solvent scavengers in the system at high HF.(See Table 2).

Another line of evidence indicating that the reaction is of the $S_N2$ type when HF concentration is below 55% is by following the quantity of benzyldimethylsulfonium salt, $C_6H_5CH_{2\text{-}S}{}^+\text{-}(CH_3)_2$. As shown in FIG. 5, the amount of sulfonium salt was inversely proportional to the 3-benzyltyrosine side product. Thus when 3-benzyltyrosine was observed to be small (0.4–2.0%) at low HF concentrations, the sulfonium salt concentration was high (between 90 to 100%). At the change-over point of the mechanism (about 55% HF) the concentration of the sulfonium salt decreased rapidly and reached 1 to 5% when the HF concentration was above 60%. Since the benzyldimethylsulfonium salt was derived from the nucleophilic displacement of the protonated benzyl ether linkage by the unprotonated dimethylsulfide, it becomes a quantitative measure of the acidity of the HF-dimethylsulfide solvent system and hence the "indicator system" for the $S_N2$ or $S_N1$ mechanism. In the final analysis, at HF concentrations below 55%, the dimethylsulfide was largely unprotonated and participated as a nucleophile while at higher HF concentrations, it is largely protonated and therefore ineffective.

TABLE 2
EFFECT OF SCAVENGER/SOLVENT IN SUPPRESSING TYROSINE ALKYLATION

| Condition | |
|---|---|
| HF | 42 |
| HF—Dimethylsulfide (9:1, v/v) | 27 |
| HF—Anisole (9:1, v/v) | 25 |
| HF—p-Cresol (9:1, v/v) | 9 |
| HF—Thioanisole (9:1, v/v) | 6 |
| TFMSA—TFA (1:4, v/v) | 42[1] |
| TFMSA—TFA—Anisole (1:40:1.2, v/v/v) | 13 |
| TFMSA—TFA—Thioanisole (1:40:1.2, v/v/v) | 1[1] |
| 4 N HBr—TFA[2] | 11[2] |
| 4 N HBr—TFA—p-cresol | 1[2] |

[1]Y. Kiso et al. Chem. Pharm. Bull 25, 2562–2564 (1978).
[2]M. Bodanszky et al. Int. Peptide and Protein Res., 12, 57–68 (1978).

In sum, at the low HF concentration range the bimolecular mechanism dominates with the unprotonated dimethylsulfide offering nucleophilic assistance, while at high HF the strong protonating properties of HF prevail, to give a strong carbocation character in the transition state and hence a monomolecular mechanism. In this respect, the effect of $S_N2$ character of acid solvent systems to deprotect Tyr(Bzl) giving little alkylation side products can be seen in Table 2. Systems with more $S_N2$ character, such as HBr-trifluoracetic and trifluoromethane sulfonic acid-trifluoroacetic-thioanisole generally provide less alkylation side products.

In theory, the HF concentration in DMS should be kept as low as possible to give a predominantly bimolecular nucleophilic character to the reaction mechanism in the deprotection mixture. However, at very low HF concentration the protonating property of the mixture is too poor to be efficient, as shown in the cleavage of O-benzyltyrosine in FIG. 5. Based on this, it is concluded that a 25% volume of HF in dimethysulfide offers a reasonable compromise to the problem. This somewhat arbitrary binary mixture offers quantitative cleavage of most benzyl alcohol-derived protecting groups, but provides only 0.4% of 3-benzyltyrosine alkylated product in the cleavage of O-benzyltyrosine.

Other tyrosine protecting groups have also been examined at low HF concentrations. 2-Bromobenzyloxy carbonyl-tyrosine was totally deprotected. 2,6-dichlorobenzyl tyrosine was only partially deprotected, and O-cyclohexyltyrosine was relatively stable at 0° C. for one hour. However, in the case of 2-bromobenzyloxycarbonyltyrosine, no or little alkylated product was observed during the deprotection by the new procedure (Table 2). The inability of low concentration of HF in dimethylsulfide to completely or partially deprotect the sterically hindered 2,6-dichlorobenzyl and cyclohexyl protecting groups reflects on the selectivity of the reagent.

EXAMPLE 3

Synthesis of Methionine-Enkephalin

The application of the new cleavage method is exemplified by the synthesis of methionine-enkephalin (3):

H-Tyr-Gly-Gly-Phe-Met-OH    (3)

The protected peptides:

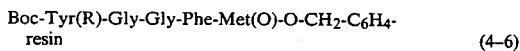

Boc-Tyr(R)-Gly-Gly-Phe-Met(O)-O-CH$_2$-C$_6$H$_4$-resin    (4–6)

were synthesized on a chloromethyl resin by the solid-phase peptide method. Three phenolic tyrosine protecting groups were chosen as models in the synthesis of Met-enkephalin to evaluate different synthetic strategies. In peptide (4) (R=Bzl), O-benzyl tyrosine was used to represent as the model for the synthesis of a relatively small peptide (<10 residues); in peptide 5 (R=2-bromobenzyloxycarbonyl) was used for the simulated model peptide for the synthesis of moderate size peptides (<30 residues). These considerations are based on the acidolytic lability of O-benzyl tyrosine ($k=6.4\times10^{-6}$ sec$^{-1}$ in 50% trifluoroacetic acid), and the basic and nucleophilic lability of 2-bromobenzyloxycarbonyl in repetitive sequential peptide synthesis. Both protecting groups will pose danger of being deprotected during the synthesis with the consequence of initiating side-chain branching and complicating the purification step at the end of the synthesis. In peptide 6 (R=2,6-dichlorobenzyl) 2,6-dichlorobenzyl tyrosine was chosen as the alternative model for the protecting group for the synthesis of a moderate length peptide. The 2,6-dichlorobenzyl protecting group is about 100 times more stable than the benzyl protecting group in trifluoroacetic acid, and is quite resistant to basic and nucleophilic conditions used in the peptide synthesis.

The model peptides 4–6 were deprotected and removed from the resin support by two conditions: A: the normal high HF concentration (HF:anisole, 9:1, v/v) followed by the thiolytic reduction of methionine sulfoxide to methionine residue by 0.2M mercaptoethanol at 37° C. for 2 days, and B: the new cleavage condition of low concentrations of HF (HF:dimethylsulfide:p-cresol 25:65:10, v/v/v). The latter condition would also concomitantly reduce methionine sulfoxide to methionine, and thus render the thiolytic reduction unnecessary. The addition of p-cresol, which swelled the peptidyl resin in HF, was necessary to give high cleavage yields. The crude products were directly analyzed by reverse phase HPLC. All four peptides of interest: Met—, Met(O)—, Tyr(R)— and Tyr(R), Met(o)-enkephalin were well separated. Thus, the amount of tyrosine alkylated side product and the purity of the crude product could be readily assessed. Furthermore, these results were also corroborated by the ion-exchange chromatography of the crude peptides and the quantitation of the 3-alkyltyrosine of the amino acid hydrolyzate by ion-exchange chromatography. The results are summarized in Table 3.

the low HF treatment was extended to two hours, and was followed by a high HF cleavage reaction for 0.5 hour. By this procedure, the 3-alkylated product was observed to be less than 0.5% (Table 3).

The protected methionine-enkephalin peptide-resin 4 was also cleaved by the HF-trifluoroacetic acid-dimeth-

TABLE 3

Results of HF Cleavage of Enkephalin Peptide-Resins 4 to 6

| | Cleavage Method | | | | | | |
|---|---|---|---|---|---|---|---|
| | A = HF:anisol (9:1, v/v) | | | | B = HF:Dimethylsulfide (1:3, v/v) | | |
| | HPLC anaylsis of peptide (mol %) | | Amino acid Anaylsis (mol %) | | HPLC anaylsis of peptide (mol %) | | Amino Acid Analysis (mol %) |
| Peptide | Enk | Tyr(R)Enk | Tyr | Tyr(R) | Enk | Tyr(R)Enk | Tyr | Tyr(R) |
| 4 (Bzl) | 70 | 30 | 72 | 28 | 99.5 | <0.5 | 99.5 | 0.5 |
| 6 (Cl$_2$—Bzl) | 95 | 5 | 95 | 4 | 99.7 | <0.3 | 99.7 | 0.3 |
| 5 (2-BrZ) | 100 | N.D.* | 99.7 | 0.3 | 100 | N.D. | 100 | 0 |

*N.D = Not detected (<0.2%)

The cleavage of Tyr(Bzl)-Met(O)-enkephalin-resin, 4, by either HF-anisole or HF-dimethylsulfide agreed well with the results on Tyr(Bzl) alone, as shown supra. The high HF method gave about 30% 3-alkylated product, and the low HF method gave 0.5% 3-alkylated product. In all of the low HF cleavage methods, it was found necessary to institute a short but milder high concentration cleavage step to complete the removal of peptide from the resin. This is carried out by removing the HF and dimethylsulfide in a vacuum, and recharging the vessel with HF so that HF-p-cresol is about 80:20 (v/v) for an additional 0.5-1.0 hour treatment at 0° C. Such treatment would generally not affect the analysis of the alkylation side reaction, since all of the O-benzyl tyrosine protecting groups are removed and inactivated at the low HF cleavage condition.

The cleavage of Tyr(2-Br-Z)-Met(O)-enkephalin-resin, 5, produced little or no alkylation product by either cleavage method (Table 3). The reason for this observation is not immediately apparent since the bromobenzyl carbocation is generated in the $S_N1$ high HF concentration, and since evidence has accumulated that alkylation reactions occurs mainly intermolecularly. Furthermore, in the best scavenging system any $S_N1$ cleavage of benzyl alcohol derived phenolic ether protecting groups results in a statistical amount of alkylation. One explanation for the results with 2-bromobenzyloxycarbonyl protecting groups for tyrosine is that at high HF deprotection, the tyrosine exists as the carbonic acid ester in which the phenyl ring is completely deactivated. The intermediate carbonic acid serves as an effective temporary protecting group for the tyrosine, to prevent alkylation on the tyrosine aromatic ring. The reactivity of the tyrosine intermediate to carbocation is difficult to establish, but the existence of the 2-bromobenzyl carbocation was established by using tyrosine as scavenger in the cleavage of peptide, 5, and 14 mole percent of 3-bromobenzyl tyrosine was found by ion-exchange chromatography. The postulated carbonic acid derivative is presumed to decompose slowly to tyrosine residue and $CO_2$ as HF is evacuated.

The cleavage of Tyr(2,6-dichlorobenzyl)-Met(O)-enkephalin-resin, 6, by method A produced the expected results of about 5% 3-alkylated product. Since the dihalogenated protecting group is very acid stable, ylsulfide system. In this study, peptide-resin 4 was first deprotected by the low HF-TFA concentration condition (HF:TFA:DMS:p-cresol: 28:12:50:10, v/v/v/v) for 2 h at 0° C. The dimethylsulfide was then removed under vacuum and the peptide-resin was further treated with the high HF-TFA concentration condition (HF:TFA:p-cresol: 28:62:10, v/v/v) for 0.5 h at 0° C. In both treatments, the HF concentrations were kept at 28% and only the TFA concentrations were changed. This has the similar effect of treating the sample at low and high HF concentrations as described. This can be better understood in the equilateral triangle diagram shown in FIG. 1. The first treatment (HF:TFA:DMS:p-cresol: 28:12:50:10, v/v/v/v) lies within the $S_N2$ sector, but as the TFA concentration increases and potentiates the acidity of HF, it crosses the changeover point curve to the $S_N1$ sector. Thus, the second treatment of HF:TFA:p-cresol: 28:62:10 v/v/v, will enable the complete removal of more acid-stable protecting groups. Alternatively, 1.0 ml commercially available 70% HF-pyridine solution, plus 1.25 ml of DMS, and 0.25 ml of p-cresol for 1 h, followed by the addition of 2.5 ml of trifluoroacetic acid for 2 h will produce the same result.

The methionine-enkephalin product was precipitated with cold ether and analysis of the crude product indicated the amount of alkylated tyrosine product was low (1.0%).

These studies on the three tyrosine protecting groups in the synthesis of methionine enkephalin by solid phase further illustrate that the new cleavage method is suitable for these protecting groups in different synthetic strategies of peptide synthesis.

EXAMPLE 4

Deprotection of $N^i$-Formyl Tryptophan to Tryptophan

In investigations of high HF concentration solutions (HF about 90%) with nucleophilic scavengers to reduce HF catalyzed side reactions, it has been found that when 10% p-thiocresol alone or as p-cresol mixture was added as scavenger to HF, $N^i$-Formyl protecting groups of tryptophan were partially deprotected to tryptophan. Similarly, other thiols such as thiophenol, ethanethiol or ethanedithiol also led to some deprotection (Table 4).

TABLE 4

Deprotection of $N^i$—Formyl Tryptophan and $N^i$—Formyl-Tryptophan-containing Peptides in HF—Dimethylsulfide-p-Thiocresol Mixtures

| Sample | Composition (volume percent)[1] | | | | Products (mol %)[2] | | |
|---|---|---|---|---|---|---|---|
| | HF | DMS | Thiol | p-cresol | Trp | Trp(For) | Side Product |
| Boc—L-Trp(For) | 90 | 5 | 0 | 5 | 2 | 98 | 0 |
| | 90 | 0 | 5[3] | 5 | 56 | 44 | 0 |
| | 90 | 0 | 5[4] | 5 | 29 | 71 | 0 |
| | 90 | 0 | 5[5] | 5 | 36 | 32 | 32 |
| | 75 | 15 | 5[5] | 5 | 78 | 19 | 3 |
| | 25 | 65 | 5[5] | 5 | 85 | 15 | 0 |
| Boc—Lys(Z)Trp(For)—Lys(Z)—OCH$_2$—R[7] | 25[6] | 65 | 5[5] | 5 | 95 | 5 | 0 |
| Boc—Gly—Trp(For)—Met(O)— | 25 | 65 | 5[5] | 5 | 100 | 0 | 0 |
| Asp(OBzl)—Phe—NH—R[7] | 25 | 65 | 5[5] | 5 | 100 | 0 | 0 |

[1]All conditions are at 0° C., 1 h unless specified; percents are expressed by volume ratio
[2]Analyzed by ion-exchange chromatography
[3]ethanethiol
[4]ethanedithiol
[5]p-thiocresol
[6]Reaction done at 0° C., 2 h
[7]Peptide was first treated with low HF concentration at 0° C. for 2 hours and then HF was raised to 90% for 1 hour at 0° C. to remove peptide from resin (R).

When HF was maintained at 90% by volume and 5 to 10% of aromatic thiols were added to the strong acid mixture, several side products besides the starting material and the deprotected $N^i$-formyl tryptophan could be identified. Preliminary results indicate that these were thiolytic addition products to Trp(For) residues. With free, unprotected Trp residues, no side reactions were observed. Alkyl-thiols such as ethanedithiol were found to polymerize extensively in HF and gave poor recovery yield of Trp-containing peptides. This was also found to be true when trifluoromethanesulfonic acid-trifluoroacetic acid was used as the acid medium. Dimethylsulfide or thioanisole was not effective.

However, when 2.5% to 10% of thiol was added to the low concentration HF-dimethylsulfide mixture, quantitative removal of $N^i$-formyl of Trp(For) was observed (Table 4). Furthermore, side products that were observed in high concentration of HF/thiol mixtures were not found during the low HF/dimethylsulfide/thiol mixtures. This further confirmed that the thiol addition side reaction to Trp(For) occurred only in high HF concentration. Thus, when $N^i$-formyl was completely deprotected in the low HF/dimethylsulfide/thiol mixture, further exposure to high concentration HF in the presence of aromatic thiol did not produce this side reaction. The best thiolytic deprotecting mixture was found to be HF/p-cresol/p-thiocresol/dimethylsulfide (25:5:5:65, v/v/v/v). In this mixture, Trp(For) or Trp(For)-containing peptides were quantitatively converted to Trp-containing peptides. Furthermore, no t-butylated tryptophan product was observed even when the deprotection was carried out in the presence of t-butyl cation sources such as Boc-Trp(For).

Figure 6:
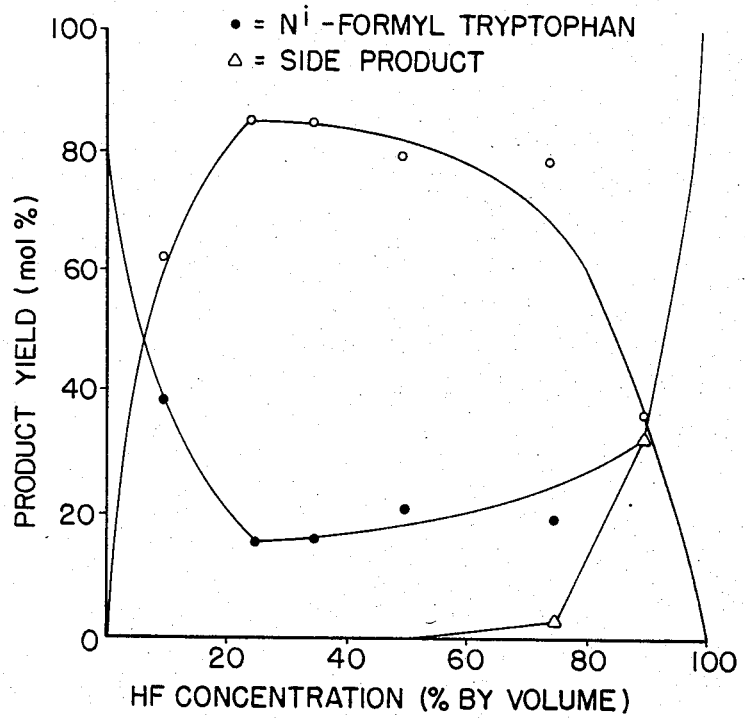
FIG. 6 demonstrates the dependence of deprotection of $N^i$-formyl tryptophan by various concentrations of HF in dimethylsulfide, in the presence of p-thiocresol, maintained at 5% by volume.

The low HF-dimethylsulfide-thiol deprotection condition, when HF concentrations were maintained between 20-40%, was found to be of near optimal acidity function, to provide for the removal of $N^i$-formyl groups and prevent other side products (see FIG. 6). With HF concentrations above or below this value, the deprotection was either too slow or side reactions occurred. When the weaker trifluoroacetic acid was substituted for HF, the deprotection of $N^i$-formyl tryptophan was found to be too slow.

EXAMPLE 5

Synthesis of C-terminal Pentapeptide Amide of Gastrin

To illustrate the efficacy of the new deprotecting method, the C-terminal pentagastrin amide 7:

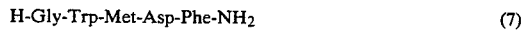

H-Gly-Trp-Met-Asp-Phe-NH$_2$        (7)

was synthesized on a multidetachable benzhydrylamine resin by the solid phase method. This difficult sequence entails four synthetic problems: The alkylation of tryptophan and methionine residues, aspartimide formation and low cleavage from the amide resin. The fully protected peptide resin 8:

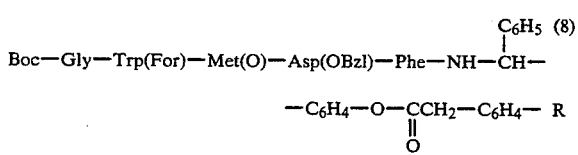

in which Trp was incorporated as Trp(For), and methionine as sulfoxide, was prepared. Deprotection of 8, first by the low concentration HF solution (HF/dimethylsulfide/p-thiocresol/p-cresol 25:65:5:5 v/v/v/v) for 2 hours at 0° C., followed by further treatment in HF at 0° C. for 1 hour, in which the HF concentration was raised to a high concentration (HF/p-cresol/p-thiocresol, 80:10:10), provided pentagastrin peptide amide 7 in 90% yield.

Both $N^i$-formyl of tryptophan and sulfoxide of methionine were removed and reduced in the single procedure. The crude peptide emerged as a major single peak in the reverse phase HPLC and ion-exchange chromatography and its purity was evaluated as greater than 95%. Comparatively, when peptide resin 8 was treated with the usual condition of HF-anisole (9:1 v/v) for 1 hour at 0° C., followed by aqueous basic deformylation procedures and thiolytic reduction of sulfoxide, the desired product was only partially pure and several major by-product peaks were obtained in the same chromatographic analyses.

EXAMPLE 6

Studies on the Reduction of Methionine Sulfoxide to Methionine

As shown in Table 5, methionine sulfoxide was found to be stable to the usual strong acid deprotection reagents HF-anisole or HF-p-cresol.

TABLE 5

| Reduction of Boc-Met(O) to Met by HF and Reductant | |
|---|---|
| Reagent (% by volume) | Yield Met (mol %) |
| HF—anisole (90:10) | <0.5 |
| HF—p-cresol (90:10) | <0.5 |
| HF—p-thiocresol (90:10) | 3 |
| HF—Dimethylsulfide (25:75) | 100 |
| HF—tetrahydrothiophene (25:75) | >99.5 |
| HF—1,4-thioxane (25:75) | <0.5 |
| HF—phenylsulfide (25:75) | 0 |
| HF—thioanisole (25:75) | 100[1] |
| HF—DMS-p-cresol-thiocresol (25:65:5:5, v/v) | >99.5% |

[1]100% reduced, but isolated product was 70 mole percent S-methylmethionine sulfonium salt, 30% Met The results indicate that neither the aromatic solvent nor the fluoride ion was nucleophilic enough to reduce methionine oxide.

In the presence of a halide acceptor such as indole or acetone, both HCl and HBr become efficient reducing agents of methionine sulfoxide by a bimolecular mechanism. When methionine sulfoxide was treated with HF-dimethylsulfide (9:1, v/v) for 1 hour at 0° C., reduction of methionine oxide to methionine was clearly observed, but only at 25–30% yield (see FIG. 7). Replacement of dimethylsulfide with the more nucleophilic thioanisole did not significantly improve the reduction yield. These results were consistent whether methionine oxide was free or incorporated into a peptide chain.

Figure 7:
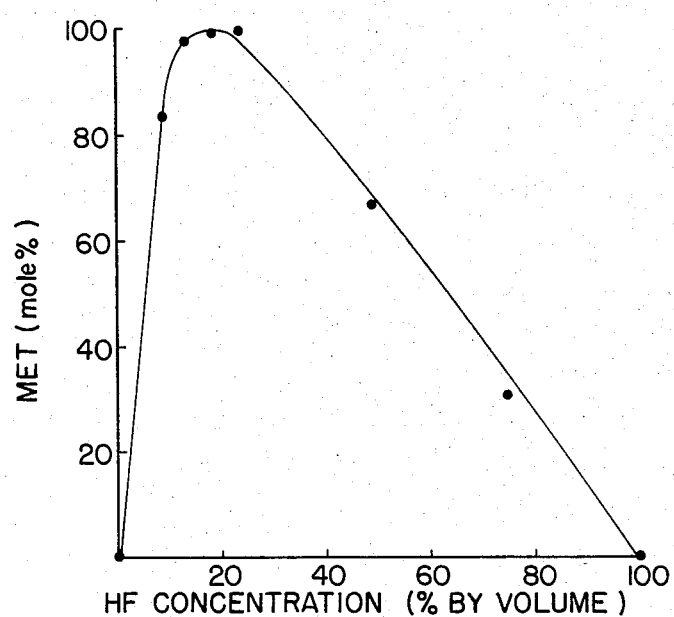
FIG. 7 demonstrates the dependence of methionine sulfoxide reduction, on the percent volume of HF in dimethyl sulfide.
Figure 8:
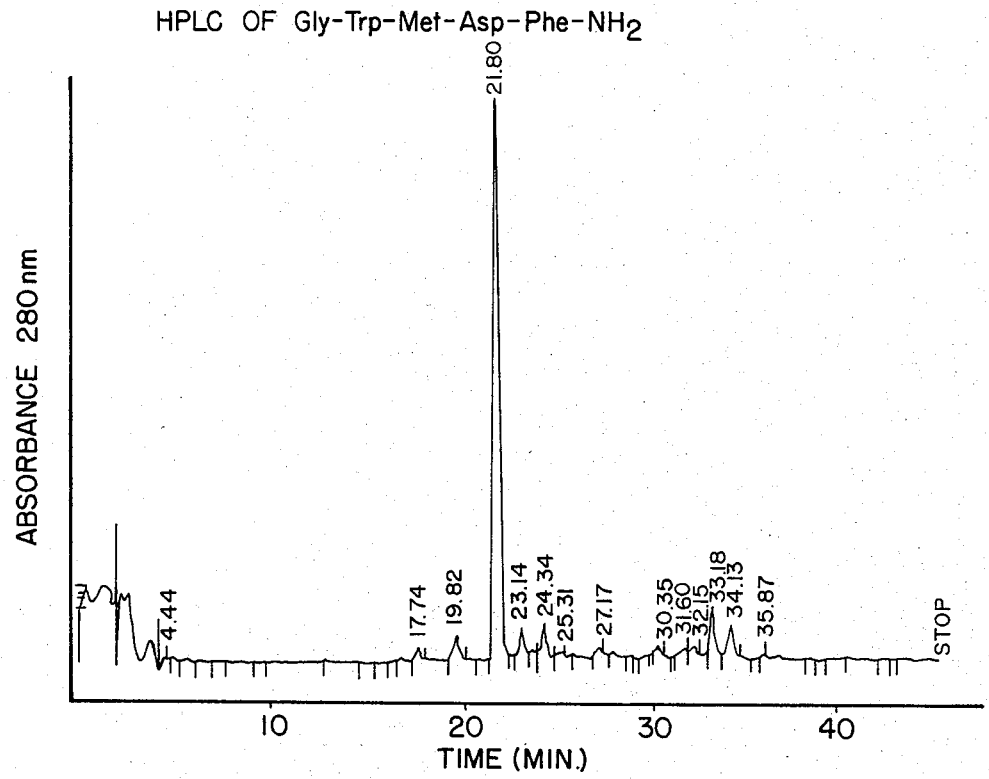
FIG. 8 demonstrates the high pressure liquid chromatographic analysis of crude pentagastrin amide on a reverse phase μBondapak C-18 column (4×300 mm), linear gradient of 2 to 98% solution B ($H_2O:CH_3CN:H_3PO_4$ 50:50:0.1, v/v/v) into solution A ($H_2O:CH_3CN:H_3PO_4$ 95:5:0.1, v/v/v), 2 ml/min. Detection at 280 nm, 0.1 absorbance full scale.

The lack of success in the reduction of methionine oxide to methionine in using high HF concentration in dimethylsulfide led to the experimentation with lower concentrations of HF. Methionine sulfoxide was treated with HF at 0° C. for 1 hour and various concentrations of dimethylsulfide (10–90%) to give different acidity functions of the HF-dimethylsulfide mixture. As shown in FIG. 7, the rate of reduction reached a maximum at 25–40% of HF in dimethylsulfide. This finding also agrees well with the basicities of sulfoxide and sulfide which have pka's of −2 and −6 respectively. The observed Ho value of 25% HF in dimethylsulfide, using Hammett indicators, was found to be about −4.6 to −5.2. Thus, when HF is lower than 25%, the Ho of the HF-dimethylsulfide solution falls, and the sulfoxide is not sufficiently protonated to allow an effective rate of reduction. When HF is higher than 40%, Ho is too high and both sulfoxide and sulfide are strongly protonated, which inhibits the reduction.

Other sulfides and thiols were also examined in the HF/disulfide reduction of methionine sulfoxide. Thioanisole was as effective as dimethylsulfide in the reaction (see Table 5). However, it has been found that in HF, thioanisole is also an alkylating agent. The reduced methionine was observed to be alkylated to S-methylmethionine at a rate of about 70% per hour. This side reaction was not found in HF/dimethylsulfide. The more basic tetrahydrothiophene was also found to be effective but the 6-member oxa-ring 1,4-thioxane, was found to be ineffective. Since HF/dimethylsulfide could be removed in vaccuo effectively, while other HF-sulfide mixtures remained as solids, complicating work up, HF-dimethylsulfide (1:3, v/v) was the reagent of choice.

EXAMPLE 7

Synthesis of the Antibacterial Peptide Cecropin A(1-33)

The new cleavage method was further tested on the synthesis of Cecropin A(1- 33). The cecropins are a newly discovered class of antibacterial peptides produced by the humoral immune response of certain insects (D. Hultmark, D., et al (1980) European Journal of Biochem. 106, 7–16). They are effective against a variety of gram negative insect pathogens but have no effects on insect cells in tissue culture or sheep erythrocytes. The structure of Cecropin A(1-33) is shown in Formula 9:

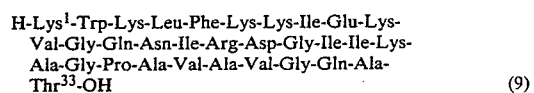

H-Lys$^1$-Trp-Lys-Leu-Phe-Lys-Lys-Ile-Glu-Lys-
Val-Gly-Gln-Asn-Ile-Arg-Asp-Gly-Ile-Ile-Lys-
Ala-Gly-Pro-Ala-Val-Ala-Val-Gly-Gln-Ala-
Thr$^{33}$-OH     (9)

The peptide was synthesized on a modified resin with a more acid-stable benzyl ester linkage (Pam resin; aminoacyl-4-(oxymethyl)phenylacetamidomethyl-copoly(styrene-divinylbenzene) resin). The structure of the synthetic protected peptide resin is shown in formula 10:

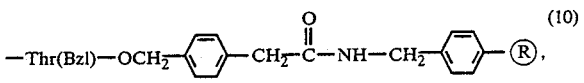

where
ClZ is 2-chlorobenzyloxycarbonyl,
For is N$^i$-formyl,
Bzl is benzyl,
Tos is tosyl, and
cHex is cyclohexyl.

The synthesis followed the stepwise solid phase strategy with the acid-labile tert-butyloxycarbonyl group for the temporary N$^\alpha$- protecting group and the more acid-stable benzyl groups for protection of the side chain. The β-cyclohexyl ester of Boc-aspartic acid (J. P. Tam, et al. Tetrahedron Lett. 4033–4036, 1979) was used to minimize aspartimide formation and tryptophan was protected with the N$^i$-formyl group. The fully protected peptide resin (150 mg) was thoroughly washed by methylene chloride and the Boc-group was removed by treating with 5 mL of 50% trifluoroacetic acid/methylene chloride containing 0.1% of ethanedithiol for 1 min and then with 5 mL of a fresh solution of the same solvent for 20 min at ambient temperature. After washing with methylene chloride, the sample was neutralized with 5% diisopropylethylamine in methylene chloride, washed with methylene chloride, pumped dry, and transferred to the reaction vessel of an HF apparatus. p-Cresol (0.5 mL), p-thiocresol (0.5 mL) and dimethylsulfide (6.50 mL) was added and 2.5 mL of anhydrous HF was condensed at −78° C. The vessel was warmed in a thermostated bath to 0° C. and the sample stirred at 0° C. for 2 h. The acid and dimethylsulfide was evaporated at 0° C. first with a water aspirator and then with a high vacuum pump. The sample was then chilled again to −78° C. and HF was then condensed to the 10 mL mark (approximately 8 mL of HF was collected). The vessel was warmed to 0° C. and sample was stirred for 45 min. The acid was evaporated with a water aspirator and then with a high vacuum. The purpose of this two step procedure was first to remove most of the protecting groups under the inventive $S_N2$ cleavage conditions which prevent alkylation side reactions, and at the same time totally deprotect Trp(For) to Trp. Finally, the high HF concentration allows the complete removal of the more acid-resistant tosyl and cyclohexyl groups.

The product was extracted with 10% acetic acid in water, and cresol and thiocresol were removed by extraction with EtOAc. The yield based on amino acid analysis was 80%. The high-performance Liquid Chromatography (HPLC) analysis of this crude and unpurified product on a μBondapak C-18 reverse phase column (FIG. 9A) revealed a single peak at 13.5 min of 93.5% purity. No other peaks at level higher than 2% were detected. The sample was applied at a high concentration, sufficient to detect impurities at the 1% level. The crude peptide was purified by chromatography on CM-sepharose, and amino acid analyses of an HCl hydrolysate as well as enzymatic digest of the purified product were in good agreement with theory. Furthermore, the purified product was homogeneous by ion-exchange chromatography, HPLC (FIG. 9B) and gel electrophoresis. Sequence analysis of the peptidyl-resin also unequivocally confirmed the sequence of the synthetic chain shown in Formula 9 and there was no evidence for the presence of any other sequence in the product. The synthetic product was about 50% biologically active as the longer amino acid sequence of natural cecropin A. The application of the new cleavage method on the synthesis of Cecropin A(1–33), a relatively difficult and complicated peptide, reveals that the new method can be used on such peptides without any detectable side reactions. The purity yield of 93.5% of the crude peptide was unmatched by any synthesis of similar size peptide to date.

EXAMPLE 8

Synthesis of Glucagon and [Tyr$^{22}$]Glucagon

Glucagon (Formula 11) and [Tyr$^{22}$]glucagon (Formula 12) were synthesized by stepwise approach on a polymeric support.

H-His-Ser-Gln-Gly-Thr-Phe-Thr-Ser-Asp-Tyr-Ser--
Lys-Tyr-Leu-Asp-Ser-Arg-Arg-Ala--
-Gln-Asp-X$^{22}$-Val-Gln-Trp-Leu-Met-Asn-Thr-
OH

(11) X=Phe
(12) X=Tyr

The new cleavage method was used at the final step of the synthesis. This is an interesting test of the method, since of the 29 amino acid residues in glucagon, 22 are trifunctional and therefore present special synthetic difficulties. Notable among these are the single residues of tryptophan, methionine and histidine, the 2 tyrosines, the 3 aspartic acids and glutamines and the problem sequences of aspartyl-serine and asparaginylthreonine. Despite several successful total syntheses of glucagon, the chemical synthesis of glucagon remains a formidable challenge. All successful syntheses attempted so far pointed to the key factor of avoidance of strong acid such as HF as the final step. The present synthesis was designed to test the new method and its use in the final step of the synthesis. The protected peptide resin is shown in formulae 13 and 14.

Boc-His(Dnp)-Ser(Bzl)-Gln-Gly-Thr(Bzl)-Phe-
Thr(Bzl)-Ser(Bzl)-Asp(OcHex)-Tyr(BrZ)-
Ser(Bzl)-Lys(2ClZ)-Tyr(BrZ)-Leu-Asp(OcHex)-
Ser(Bzl)-Arg(Tos)-Arg(Tos)-Ala-Gln-Asp(O-
cHex)-X$^{22}$-Val-Gln-Trp(For)-Leu-Met(O)-Asn-
Thr(Bzl)-OCH$_2$- R

(13) X=Phe
(14) X=Tyr(BrZ)

Figure 11:
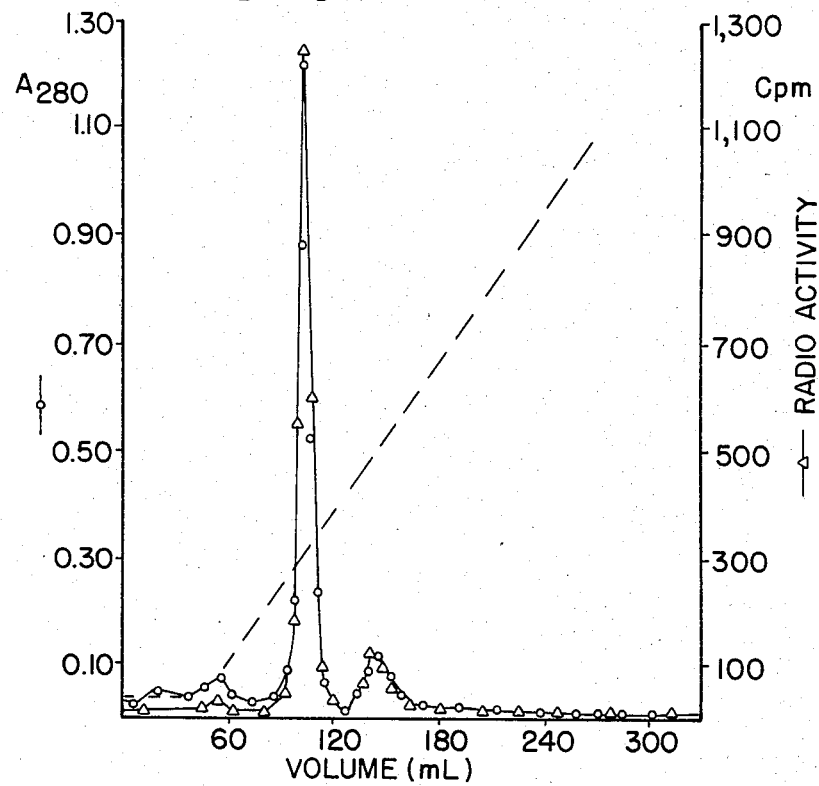
FIG. 11 demonstrates the DEAE-Sephacel chromatographic analysis of crude (Tyr[22]) glucagon after HF cleavage by the improved method of the invention. Elution with a linear gradient of 0.01M Tris in 6M urea, 0.3N NaCl (Buffer B) to 0.01M Tris in 6M urea (Buffer A). 0.3 ml/mn. Detection by radioactivity (—△—) ($10^3$ cpm) and absorbance at 280 nm (—0—)
Figure 13:
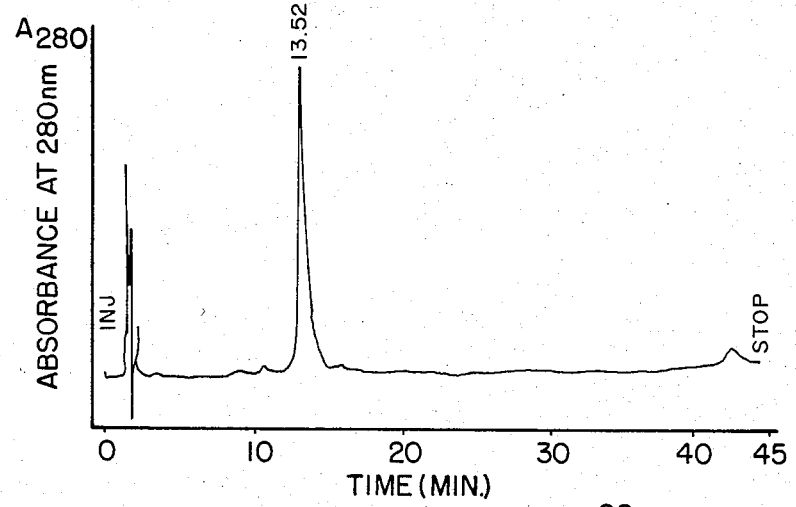
FIG. 13 demonstrates the high pressure liquid chromatographic analysis of purified (Tyr[22]) glucagon on a reverse phase μBondapak column (4×300 mm). Conditions similar to those in FIG. 11
Figure 12:
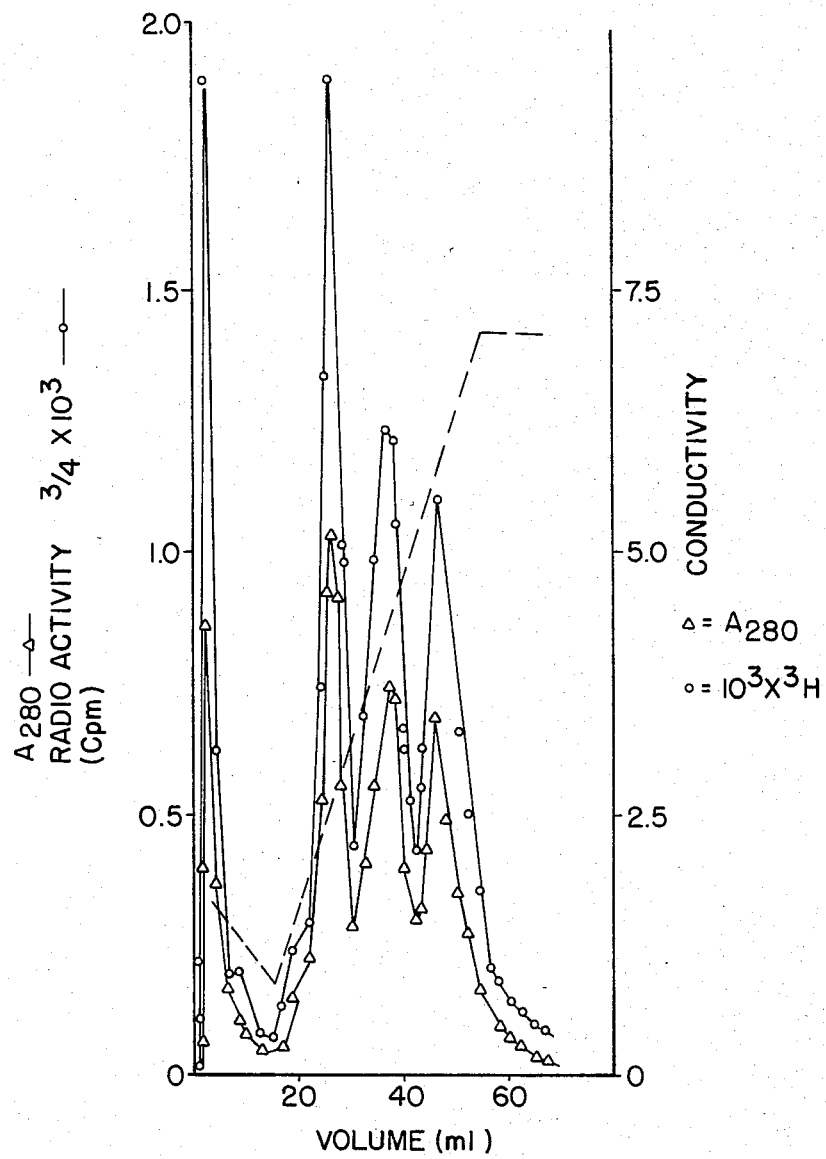
FIG. 12 demonstrates the CM-52 chromatographic analysis of crude (Tyr[22]) glucagon after HF cleavage by the standard method (HF-p-cresol 9:1, v/v). Elution with a linear gradient of 0.1M ammonium acetate in 6M urea (Buffer B) to 0.01M ammonium acetate in 6M urea (Buffer A). Flow rate 0.3 ml/min, detection by radioactivity (—0—), ($10^3$ cpm) and absorbance at 280 nm (—△—)

The synthesis of Glucagon and [Tyr$^{22}$]glucagon followed the strategy delineated of Cecropin A(1–33) in Example 7. The cleavage and deprotection of the peptidyl resin was similarly carried out in a two-step: (1) low HF procedure (HF:dimethylsulfide:p-cresol:p-thiocresol 25:65:5:5, v/v/v/v) for 2 h ar 0° C. and then followed by (2) high HF treatment (HF: p-cresol: p-thiocresol, 90:5:5, v/v/v) for 1 h at 0° C. Cleavage and deprotection of glucagon-resin went in 80% yield and the chromatographic purification gave purified synthetic glucagon that was indistinguishable from natural glucagon by a host of physical and biological criteria. Similarly, the deprotection of [Tyr$^{22}$]glucagon-resin went in 81% yield and the purity of the crude unpurified peptide was judged to be 72%. High performance liquid chromatography analysis of this crude product is shown in FIG. 10. The chromatograph showed 2 major peaks, one at 15 min and the other accounting for 72% of all material at 20 min. There is no other peak higher than 2% of the background. Similarly ion exchange chromatography of this crude product revealed the same two peaks (FIG. 11). As a comparison, the ion-exchange chromatography of the crude product of the same [Tyr$^{22}$]glucagon-resin removed and deprotected by usual high HF treatment alone (HF:p-cresol, 9:1 v/v) for 1 h to 0° C. revealed 4 major peaks (FIG. 12). The [Tyr$^{22}$]glucagon after purification by reverse phase high performance liquid chromatography (FIG. 13) was shown to be homogeneous by high pressure liquid chromatography, gel filtration and electrophoresis. The amino acid analysis by 6 N HCl hydrolysis and the synthetic sequence by Edman degradation of the peptidyl resin gave exellent agreement with theory. Furthermore, [Tyr$^{22}$]glucagon was found to be 70% as active as natural glucagon in a biological assay.

EXAMPLE 9

Synthesis of Human Gastrin (1–17)

The heptadecapeptide amide of human gastrin (1–17) is represented by formula 15:

Pca-Gly-Pro-Trp-Leu-(Glu)$_5$-Ala-Tyr-Gly-Trp-
Met-Asp-Phe-NH$_2$     (15)

Pca=pyroglutamic acid

It was synthesized on a polymeric support by stepwise approach in analogy to Example 8. The fully protected peptide resin 16 was prepared:

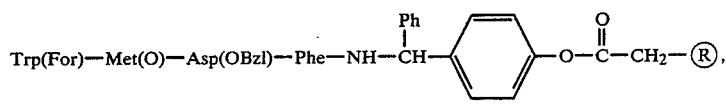

Trp(For)—Met(O)—Asp(OBzl)—Phe—NH—CH(Ph)—C6H4—O—C(=O)—CH2—(R),   (16)

where
Pca=pyroglutamic acid,
Bzl=benzyl,
For=N$^i$-formyl,
BrZ=2-bromo-benzyloxycarbonyl, and
Met(O)=methionine sulfoxide, in which Trp was incorporated as Trp(For), and methionine as sulfoxide.

Deprotection of 16 first by the low concentration HF solution (HF/dimethylsulfide/p-thiocresol/p-cresol 25:65:5:5 v/v/v/v) for 2 hours at 0° C. for 1 hour, in which the HF concentration was raised to 80%, provided human gastrin I (1–17) in 92% cleavage yield.

The crude product, without purification, was examined by HPLC and found to consist of two peaks. The peak at 4.0 min is the sulfonium salt peak. The main peak at 7.0 min which, after amino acid analysis, was the correct product, accounted for 89% of the total product. The overall yield was 80%. The crude product was purified by preparative reverse-phase HPLC and excellent agreement was obtained with theory on amino acid analysis and chromatographic behavior.

As late as 1980, the synthesis of human gastrin (1–17) by the above method and cleavage by HF produced no or little product corresponding to human gastrin (A. Scarso et al (1980) in "Peptides 1980" K. Brunfeldt ed. pp 321–325).

Complicated solution syntheses of human gastrin (1–17) have been achieved (J. Beacham et al, J. Chem. Soc. (1967) 2520), but the methodologies employed all point to the avoidance of HF as the final step. This is necessitated by the abundance of strongly acid sensitive amino acid residues in this sequence. For example, the dehydration of glutamic and aspartic acid and alkylation of tyrosine, tryptophan and methionine are well documented to be serious side reactions. In human gastrin (1–17), these amino acids account for 10 out of 17 residues. The success of the present synthesis points to the great value of the new deprotection procedure for the synthesis of complicated peptides such as gastrin.

EXAMPLE 10

Comparison of Various Reagents According to the Invention and Comparative Reagents The following Table shows a comparison of weak organic bases and their pKa's when tested at low HF concentrations in the various deprotections of the invention.

TABLE 6

| | Weak Organic Bases Tested Using Low HF Concentration | | | |
|---|---|---|---|---|
| | Effects on Protecting Groups | | | |
| Weak base (pKa) | Deprotection without alkylation e.g. Tyr(Bzl) | Reduction of Met(O) | Deprotection of Trp(For) | Dehydration of glutamic acid side chain |
| 1. phenol (−7) | Yes | No | No | No |
| 2. m-cresol | Yes | No | No | No |
| 3. p-cresol | Yes | No | No | No |
| 4. anisole | No | No | No | No |
| 5. thiophenol | | No | Yes | No |
| 6. p-thiocresol | | No | Yes | No |
| 7. 3,4-dithiotoluene | | No | Yes | No |
| 8. 1,2-dithioethane | | No | Yes | No |
| 9. ethanethiol | | No | Yes | No |
| 10. thioanisole (−7) | Yes | Yes | No | No |
| 11. dimethylsulfide (−5) | Yes | Yes | incomplete | No |
| 12. tetrahydrothiophene (−4.5) | Yes | Yes | incomplete | No |
| 13. 1,4-thioxane | No | No | No | |
| 14. Diphenylsulfide | | No | No | No |
| 15. Methionine | Yes | Yes | No | No |
| 16. dioxane + p-cresol | Yes | No | No | No |
| 17. tetrahydrofuran + p-cresol | Yes | No | No | No |
| 18. Trifluoroacetic acid p-cresol | | No | No | |
| 19. acetic acid + p-cresol | | No | No | |
| 20. triphenylphosphine | | No | No | |
| 21. tributylphosphine | | No | No | |
| 22. pyridine (5.21) | No | No | No | No |
| 23. triethylamine (11.01) | No | No | No | No |

Comments: Ideally, the best weak base should have the following properties (1) Deprotection occurs without alkylation: Yes; (2) reduction of methionine oxide: Yes; (3) deprotection of Trp(For): Yes; and (4) dehydration of glutamic acid: No.

Since no one single reagent tested may have such characteristics, a combination of reagents may be sometimes indicated. For example, dimethylsulfide and p-thiocresol may be used for a combination of effects. P-cresol is also used because it has the effect of swelling resins.

Having now fully described this invention, it will be appreciated by those of skill in the art that the same can be performed within a wide and equivalent range of parameters, conditions and reagents without affecting the spirit or scope of the invention or any embodiment thereof.

What is claimed as new and intended to be protected by Letters Patent of the United States is:

1. In a method of synthesizing peptides by the solid phase methodology, wherein the growing peptide chain is covalently attached by a functional group through a linkage having proton affinity, to the organic residue of a resin, the improvement wherein said peptide is detached from said resin using a mixture of HF and a base selected from the group consisting of di-$C_1$-$C_{10}$-alkyl sulfides and alkyl phenyl sulfides, wherein the amounts of HF and base in said mixture are adjusted so that said detachment occurs predominantly by an $S_N2$ mechanism, said HF being present in said mixture in an amount between 0.1 and 60% by volume.

2. The method of claim 1 wherein said base also serves as diluent in said mixture.

3. The method of claim 1 wherein said base has a pKa of between −2 and −11.

4. The method of claim 1 wherein said dialkylsulfide is dimethyl sulfide.

5. The method of claim 1 wherein said linkage having proton affinity is an ester, ether or carbamate linkage.

6. The method of claim 1 wherein said HF is present in said mixture in an amount sufficient to protonate at least 1% of said linkage.

7. The method of claim 1 wherein said HF is present in said mixture in an amount such that detectable amounts of unprotonated base remain in the solution.

8. The method of claim 7 wherein said base is protonated no more than 99%.

9. The method of claim 1 wherein the mixture further comprises about 1 to about 20 percent by volume of scavengers for carbocations including phenols, indoles, ethers, thioethers, thiophenols and sulfides.

10. The method of claim 1 wherein said mixture also contains 1–50% by volume of a compound capable of swelling a polymeric resin.

11. The method of claim 1 wherein said functional group is —COOH, —$NH_2$, —SH, —OH, >NH, —S— or

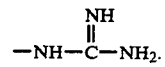

12. The method of claim 1 wherein said mixture also comprises a polar solvent.

13. The method of claim 1 wherein the organic residue of said resin is a benzyl residue.

14. The method of claim 1 wherein said resin is a polystyrene resin.

15. The method of claim 1 wherein said mixture is a binary mixture comprising HF and dimethylsulfide, wherein the HF is present in said mixture in 0.1–60% by volume.

16. The method of claim 1 wherein said mixture also contains between 1 and 10% by volume of a $C_1$-$C_{10}$ alkyl thiol or any aryl thiol.

17. The method of claim 14 wherein said mixture contains 1–20% by volume of a phenol.

18. The method of claim 1 which, after said reaction of said mixture with said peptide, comprises the additional step of reacting said peptide with HF at a concentration of greater than 60% by volume.

19. In the method of claim 1 wherein said peptide is selected from the group consisting of C-terminal-pentapeptide amide of gastrin, cecropin A (1–33), glucagon, $Tyr^{22}$-glucagon, and human gastrin (1–17).

* * * * *

UNITED STATES PATENT AND TRADEMARK OFFICE
CERTIFICATE OF CORRECTION

PATENT NO. : 4,507,230
DATED : March 26, 1985
INVENTOR(S) : James P. Tam, et al.

It is certified that error appears in the above-identified patent and that said Letters Patent are hereby corrected as shown below:

Column 14, Line 46, delete "one".

Column 24, Line 28, insert -- Boc-Lys(ClZ)-Trp(For)-Lys-(ClZ)-Leu-Phe-Lys(ClZ)-Lys(ClZ)-Ile-Glu(OBzl)-Lys(ClZ)-Val-Gly-Gln-Asn-Ile-Arg(Tos)-Asp(OcHex)-Gly-Ile-Ile-Lys(ClZ)-Ala-Gly-Pro-Ala-Val-Ala-Val-Val-Gly-Gln-Ala- --.

Column 27, Line 1, insert -- Pca-Gly-Pro-Trp(For)-Leu-(Glu(OBzl))$_5$-Ala-Tyr(BrZ)-Gly- --.

Signed and Sealed this

Eighth Day of October 1985

[SEAL]

Attest:

Attesting Officer

DONALD J. QUIGG

Commissioner of Patents and Trademarks—Designate